US006997917B2

(12) United States Patent
Niedospial, Jr. et al.

(10) Patent No.: US 6,997,917 B2
(45) Date of Patent: *Feb. 14, 2006

(54) TABLE TOP DRUG DISPENSING VIAL ACCESS ADAPTER

(75) Inventors: John J. Niedospial, Jr., Burlington, NJ (US); Jason M. Voytilla, Philadelphia, PA (US)

(73) Assignee: Bracco Diagnostics, Inc., Princeton, NJ (US)

( * ) Notice: Subject to any disclaimer, the term of this patent is extended or adjusted under 35 U.S.C. 154(b) by 7 days.

This patent is subject to a terminal disclaimer.

(21) Appl. No.: 10/958,805

(22) Filed: Oct. 5, 2004

(65) Prior Publication Data

US 2005/0124964 A1 Jun. 9, 2005

Related U.S. Application Data

(63) Continuation of application No. 09/994,543, filed on Nov. 27, 2001, now Pat. No. 6,832,994, which is a continuation-in-part of application No. 09/668,815, filed on Sep. 23, 2000, now Pat. No. 6,544,246, which is a continuation-in-part of application No. 09/489,619, filed on Jan. 24, 2000, now Pat. No. 6,139,534.

(51) Int. Cl.
*A61B 19/00* (2006.01)

(52) U.S. Cl. ...................... 604/411; 604/414; 604/403; 604/905; 206/828; 215/247

(58) Field of Classification Search ............... 604/403, 604/405, 406, 408, 411, 414, 415, 905, 533, 604/82; 206/363–366, 828; 215/247–248
See application file for complete search history.

(56) References Cited

U.S. PATENT DOCUMENTS

| | | | | |
|---|---|---|---|---|
| 4,645,073 | A * | 2/1987 | Homan | 206/219 |
| 5,125,415 | A * | 6/1992 | Bell | 600/579 |
| 5,451,374 | A * | 9/1995 | Molina | 422/99 |
| 6,544,246 | B1 * | 4/2003 | Niedospial, Jr. | 604/411 |
| 6,832,994 | B1 * | 12/2004 | Niedospial et al. | 604/411 |

* cited by examiner

*Primary Examiner*—Patricia Bianco
*Assistant Examiner*—Leslie Deak
(74) *Attorney, Agent, or Firm*—M. Caragh Noone

(57) ABSTRACT

A vial having a V-shaped bottom to minimize the amount of medical fluid left in the vial at the end of the fluid withdrawal process. The vial is equipped with a vial access adapter having a fluid withdrawal spike which extends into the V-shaped bottom. The vial access adapter may be vented or non-vented. When the medical fluid is a nuclear drug, the vial and vial access adapter is enshrouded in a protective container containing lead to provide a safety to medical personnel from irradiation.

2 Claims, 21 Drawing Sheets

TABLE TOP DRUG DISPENSING VIAL ACCESS ADAPTER

This application is a continuation of application Ser. No. 09/994,543, filed Nov. 27, 2001 now U.S. Pat. No. 6,832, 994, which is a continuation-in-part of application Ser. No. 09/668,815, filed Sep. 23, 2000 now U.S. Pat. No. 6,544, 246, which is a continuation-in-part of application Ser. No. 09/489,619, filed Jan. 24, 2000, now U.S. Pat. No. 6,139, 534.

BACKGROUND OF THE INVENTION

1. Field of the Invention

This invention relates to a vial access adapter connected to a vial which contains a medical fluid therein and is closed by an elastomeric stopper.

2. Reported Developments

Vials made of glass or polymeric materials, the walls of which are non-collapsible, require an air inlet when medical fluid is withdrawn therefrom to prevent the formation of vacuum therein. Typically, vials containing a medical fluid are closed by rubber stoppers which are pierced by a dual spike having a medical fluid passage and an air inlet passage therein. The air inlet passage contains a filter to prevent entry of particulate matter or bacteria into the vials during the medicament withdrawal process.

An improvement in the present invention over the prior art is the spatial configuration of the medical fluid access spike which, on positioning of the vial access adapter over a vial having a rubber stopper, allows essentially complete withdrawal of the medical fluid contained in the vial.

The present invention comprises at least three embodiments. In a first embodiment the medical fluid access spike penetrates the rubber stopper and just clears the bottom surface of the rubber stopper. The vial, to which the vial access adapter is attached, is turned upside down during the withdrawal process. In a second embodiment the medical fluid access spike penetrates the rubber stopper and extends to the bottom of the vial. The vial in this embodiment is held in an upright position during the withdrawal process. Both embodiments allow essentially complete withdrawal of the medical fluid contained in the vial.

A third embodiment of the present invention concerns handling large and/or heavy liquid drug containers, and specifically containers for nuclear drugs (e.g. radiopharmaceuticals). Based on safety guidelines issued by the Food and Drug Administration, including the 1991 Bloodborne Pathogens Standard (29 CFR 1910.1030) and the most recent revision to that standard (H.R. 5178), medical device manufacturers are instructed to strengthen safety requirements relating to the use of safety-engineered sharp devices. Typically, medicaments contained in vials are accessed using a steel needle or with a point-of-use needleless adapter. When vials contain nuclear imaging products it is required that shielding is in place in front of the technician who removes the nuclear products from the vial for administration to patients. In addition, it is also required that the nuclear drug itself is to be placed in a protective container, often referred to as PIG, that is constructed of lead or a lead-containing alloy. This latter requirement is difficult to meet considering, for example, that a lead PIG for a 30 ml vial could weigh up to seven pounds. Inverting the vial and inserting the steel needle to remove some or all of its contents is extremely difficult due to the weight of the PIG. Since the vial is held upside-down in the PIG cover, a means to hold the vial in the PIG is necessary so that it does not fall out by the affect of gravity. Attempts were made to hold the vial in the PIG by friction fit. However, this made the removal of the vial from the PIG unsafe and difficult due to the force required to remove the vial from the PIG. When a vial is nearly empty, the radio pharmacist has to manipulate the steel needle, whether the vial is right-side-up or upside-down, to ensure that as much of the nuclear drug as possible is removed from the vial to minimize waste.

The present invention addresses this requirement by providing a vial having a flat, concave, V-shaped bottom and a needleless access means which allow close to complete removal of the nuclear medicine contained in the vial standing right-side-up on a table top or a similar flat horizontal surface.

SUMMARY OF THE INVENTION

In accordance with a first embodiment of the present invention, there is provided a vial access adapter for use with a glass vial or a rigid or semi-rigid polymeric vial containing a liquid medicament, diagnostic agent, or nutritional formulation therein. The vial access adapter body comprises:

a horizontal top wall having a plurality of vent holes therein;

a horizontal second wall spaced parallel from the horizontal top wall;

a cylindrical side wall integral with the horizontal top wall and the horizontal second wall enclosing a chamber therebetween and extending downward from the horizontal second wall forming a skirt and terminating in a bottom rim;

a first spike centrally located in the vial access adapter body having a top portion extending above the horizontal wall and terminating in an externally threaded luer connector, and a bottom portion extending downward and terminating in a sharp point;

a fluid flow channel in the first spike designed for carrying the liquid medicament;

a second spike positioned parallel to the first spike extending downward from the horizontal second wall and terminating in a sharp point;

an air flow channel in the second spike designed for air flow from the chamber between the horizontal top wall and the horizontal second wall into the vial during withdrawal of the liquid medicament from the vial; and an elastomeric membrane within the luer connector for sealing the fluid flow channel.

Preferably, the elastomeric membrane reseals itself upon repeated penetration by an external luer connector and allows repeated withdrawal of the liquid medicament from the vial without risk of contamination from atmospheric environment.

In accordance with a second embodiment of the present invention, there is provided a vial access adapter used in combination with a glass vial or a rigid or semi-rigid polymeric vial containing a liquid medicament, diagnostic agent, or nutritional formulation therein. The vial comprises:

a cylindrical side wall;

a flat bottom portion; and a constricted neck portion terminating in a rim.

The constricted neck portion and the rim define an open area which is closed by an elastomeric stopper hermetically sealing the content of the vial. The elastomeric stopper comprises a cylindrical side wall and flat top and bottom surfaces.

The vial access adapter is designed to be placed on the constricted neck portion of the vial and to pierce the elastomeric stopper by a dual spike, one serving as a fluid flow channel and the other as an air flow channel. The vial access adapter, having a vial access adapter body, comprises:

a horizontal top wall having a plurality of vent holes therein;

a horizontal second wall spaced parallel from the horizontal top wall;

a cylindrical side wall integral with the horizontal top wall and the horizontal second wall enclosing a chamber therebetween and extending downward from the horizontal second wall forming a skirt and terminating in a bottom rim;

a first spike centrally located in the vial access adapter body having a top portion extending above the horizontal wall and terminating in an externally threaded luer connector, and a bottom portion extending downward to the flat bottom portion of the vial and terminating in a sharp point;

a fluid flow channel in the first spike adapted to carry the liquid medicament from the vial;

a second spike positioned parallel to the first spike extending downward from the horizontal second wall and terminating in a sharp point, said second spike extending just below the bottom surface of the elastomeric stopper;

an air flow channel in the second spike designed for air flow from the chamber between the horizontal top wall and the horizontal second wall into the vial during withdrawal of the liquid medicament from the vial; and an elastomeric membrane within the luer connector for sealing the fluid flow channel.

Preferably, the elastomeric membrane reseals itself upon repeated penetration by an external luer connector and allows repeated withdrawal of the liquid medicament from the vial without risk of contamination from atmospheric environment.

The vial and vial access adapter combination provides a delivery system for a medical fluid from the vial wherein the vial is in an upright position during the withdrawal process by the use of a luer-equipped syringe allowing complete or close to complete withdrawal of the medical fluid from the vial. The combination requires matching the height of the vial with the length of the fluid flow channel for complete or close to complete withdrawal of the medical fluid from the vial: each vial access adapter is “dedicated” to the particular height of the vial. If the height of the vial is not precisely matched with the length of the fluid channel flow spike, less than complete withdrawal of the medical fluid from the vial is achieved.

In accordance with a third embodiment of the present invention, there is provided a glass vial or a rigid or semi-rigid polymeric vial containing a liquid medicament, diagnostic agent, or nutritional formulation, and preferably a nuclear formulation therein. The vial comprises:

- a cylindrical side wall;
- a bottom portion having an outside wall and an inside wall wherein: said outside wall is flat, capable of being placed on a horizontal surface, such as a tabletop or a protective cylindrical container having a flat, horizontal bottom surface, and said inside wall comprises a generally V-shaped configuration having a side wall with an angle of more than 90° and less than 180° to the horizontal bottom surface and preferably an angle of about 100° to about 170°; and
- a constricted neck portion terminating in a rim.

The inside wall preferably terminates at the center bottom portion of the vial, however, it may be spaced from the center portion of the vial forming a relatively small horizontal flat surface parallel to the flat, horizontal outside wall of the bottom portion.

The constricted neck portion and the rim define an open area which is closed by an elastomeric stopper hermetically sealing the content of the vial. The elastomeric stopper comprises a cylindrical side wall and flat top and bottom surfaces.

The vial of the present invention may be equipped with a non-vented vial access adapter which is placed on the constricted heck portion of the vial and pierces the elastomeric stopper by a fluid withdrawal spike having a flow channel therein. The fluid withdrawal spike extends from the vial access adapter to the bottom of the vial and is capable of delivering most of the content of the vial which is in a right-side-up position. The vial access adapter, having a vial access adapter body comprises:

- a horizontal top wall;
- a cylindrical side wall integral with the horizontal top wall extending downward from the horizontal top wall forming a skirt and terminating in a bottom rim, said skirt is adapted to tightly engage the rim portion of the vial;
- a fluid withdrawal spike having a flow channel therein, centrally located in the vial access adapter body having a top portion extending above the horizontal top wall and terminating in an externally threaded female luer connector, and the bottom portion extending downward to the V-shaped bottom portion of the vial; and
- a removable cap covering the externally threaded female luer connector to hermetically seal the content of the vial prior to use.

The vial of the present invention is preferably equipped with a vented vial access adapter which is placed on the constricted neck portion of the vial and pierces the elastomeric stopper by a fluid withdrawal spike having a flow channel therein. The fluid withdrawal spike extends from the vial access adapter to the bottom of the vial and is capable of delivering most of the content of the vial which is in a right-side-up position. The vented vial access adapter, having a vial access adapter body comprises:

- a horizontal top wall having a plurality of vent holes therein;
- a horizontal second wall spaced parallel from the horizontal top wall;
- a cylindrical side wall integral with the horizontal top wall and the horizontal second wall enclosing a chamber therebetween and extending downward from the horizontal top wall forming a skirt and terminating in a bottom rim, said skirt is adapted to tightly engage the rim portion of the vial;
- a fluid withdrawal spike having a flow channel therein centrally located in the vial access adapter body having a top portion extending above the horizontal top wall and terminating in an externally threaded female luer connector, and the bottom portion extending downward to the V-shaped bottom portion of the vial; and
- a removable cap covering the externally threaded female luer connector to hermetically seal the content of the vial prior to use.

DETAILED DESCRIPTION OF THE INVENTION

Figure 1:
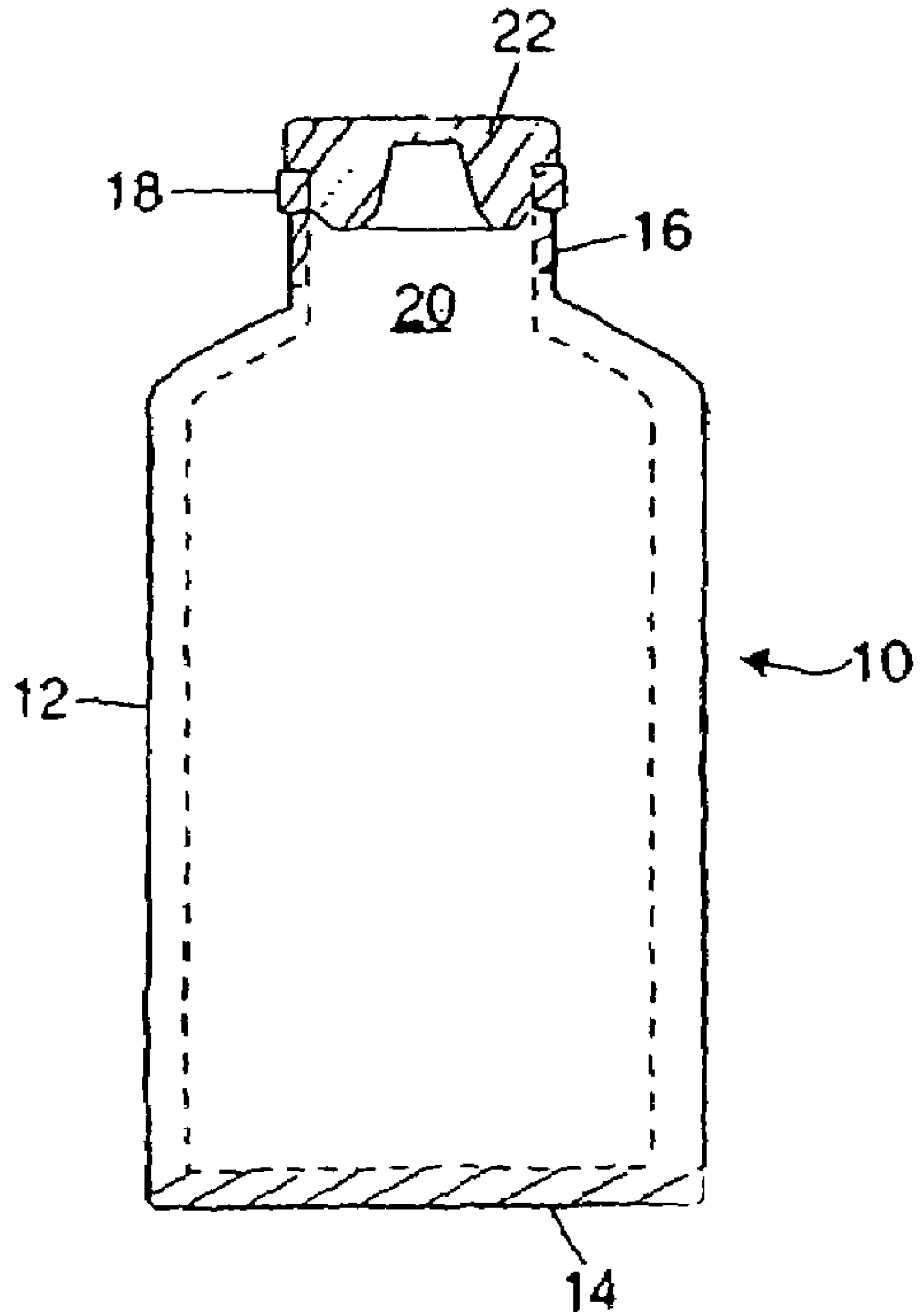
FIG. 1 is a cross-section of a typical vial used in conjunction with the vial access adapter of the present invention.

The vial access adapter of the present invention is used in conjunction with containers such as vials containing a fluid medicament therein, such as parenteral solutions and diagnostic media. Referring to the drawings, FIG. 1 shows the cross-section of vial 10 in an upright position having: a cylindrical side wall 12, a flat bottom portion 14 so that it may be placed in normal upright position on any flat surface, and a constricted neck portion 16 terminating a rim 18. The neck portion and rim define an open area 20 closed by stopper 22 hermetically sealing the content of the vial. Typically, the stopper is held in the vial by a metal band (not shown).

The present invention comprises at least three embodiments.

Figure 2:
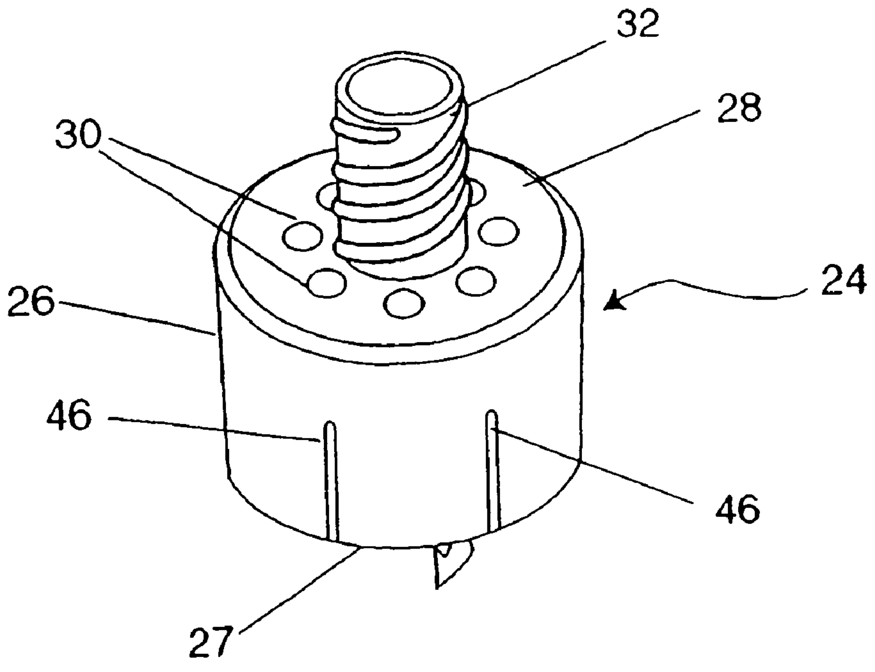
FIG. 2 is a perspective view of the vial access adapter showing the cylindrical side wall, flat top portion with vent holes, and threaded luer connector means rising above the flat top portion.
Figure 3:
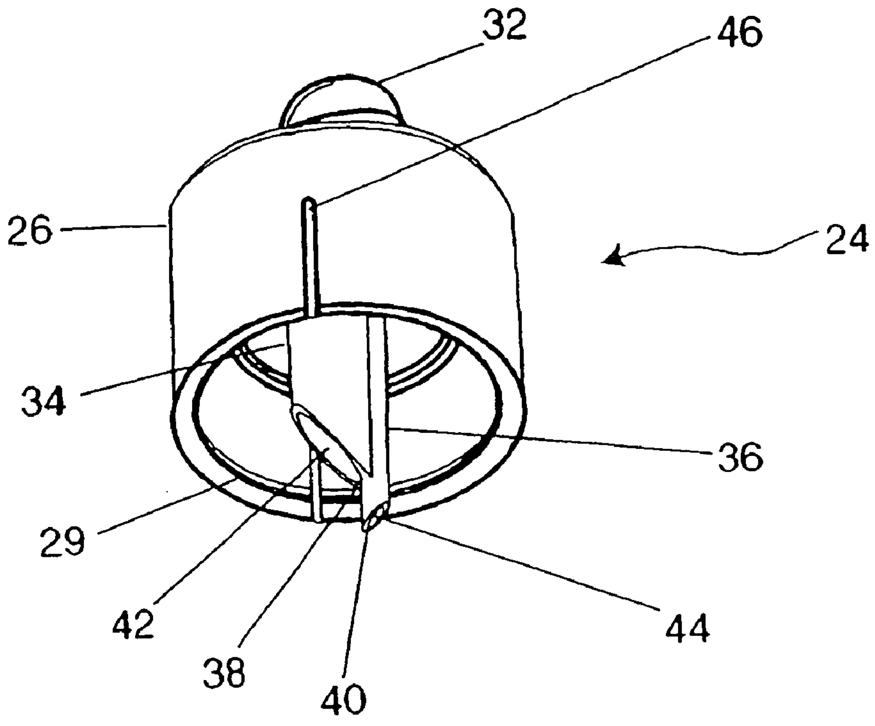
FIG. 3 is a another perspective view of the vial access adapter showing the cylindrical side wall, and the dual spike terminating in piercing sharp points.

In a first embodiment, the vial access adapter, generally designated by the numeral 24 and shown in perspective views in FIGS. 2 and 3, comprises: a cylindrical side wall 26 terminating in a rim 27; a flat, horizontal top wall 28 having vent holes 30 therein; threaded luer connector means 32 projecting vertically above the horizontal top wall 28; and a dual spike 34 and 36, terminating in sharp points 38 and 40, extending parallel to each other, and having flow passages therein 42 and 44, one being designed for passage of medicament, and the other being designed for passage of air. Cylindrical side wall 26 of the vial access adapter 24 is preferably provided with a plurality of slots 46 to facilitate the positioning of the vial access adapter onto vial 10 by a snap-on motion. In order to securely hold the vial access adapter on the vial, rim 27 of cylindrical side wall 26 is provided with protuberance 29 projecting towards dual spike 34 and 36. Protuberance 29 engages the neck portion 16 just below rim portion 18 of vial 10.

Figure 4:
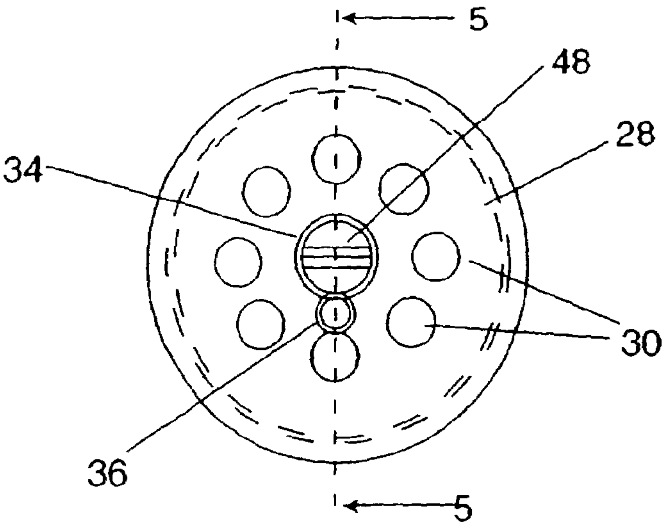
FIG. 4 is a top plan view of the vial access adapter.
Figure 5:
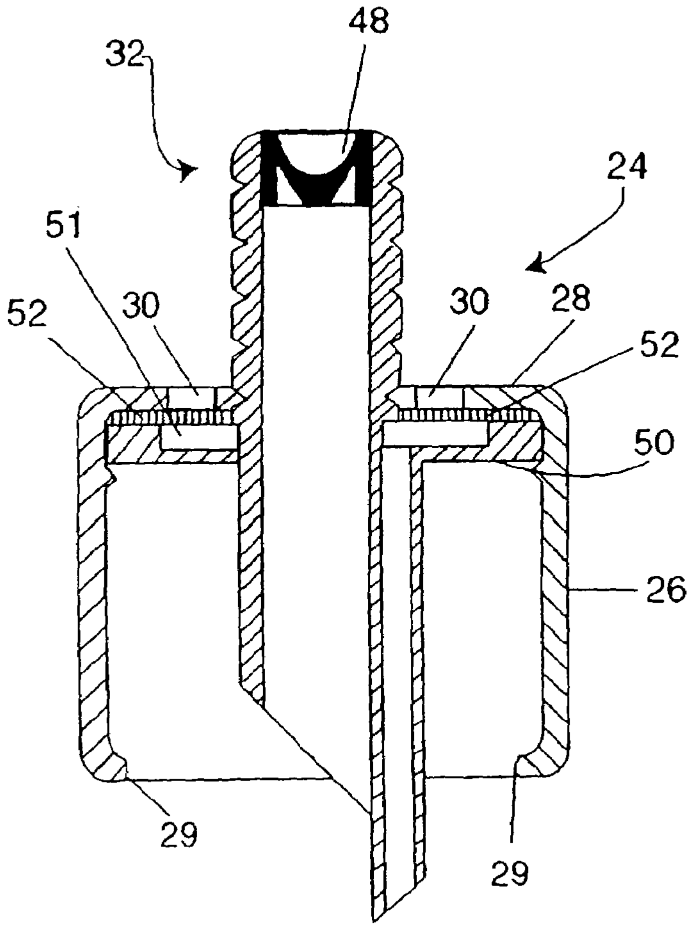
FIG. 5 is a cross-sectional view of the vial access adapter, having an M-shaped member therein, taken along the line 5—5 of FIG. 4.
Figure 5A:
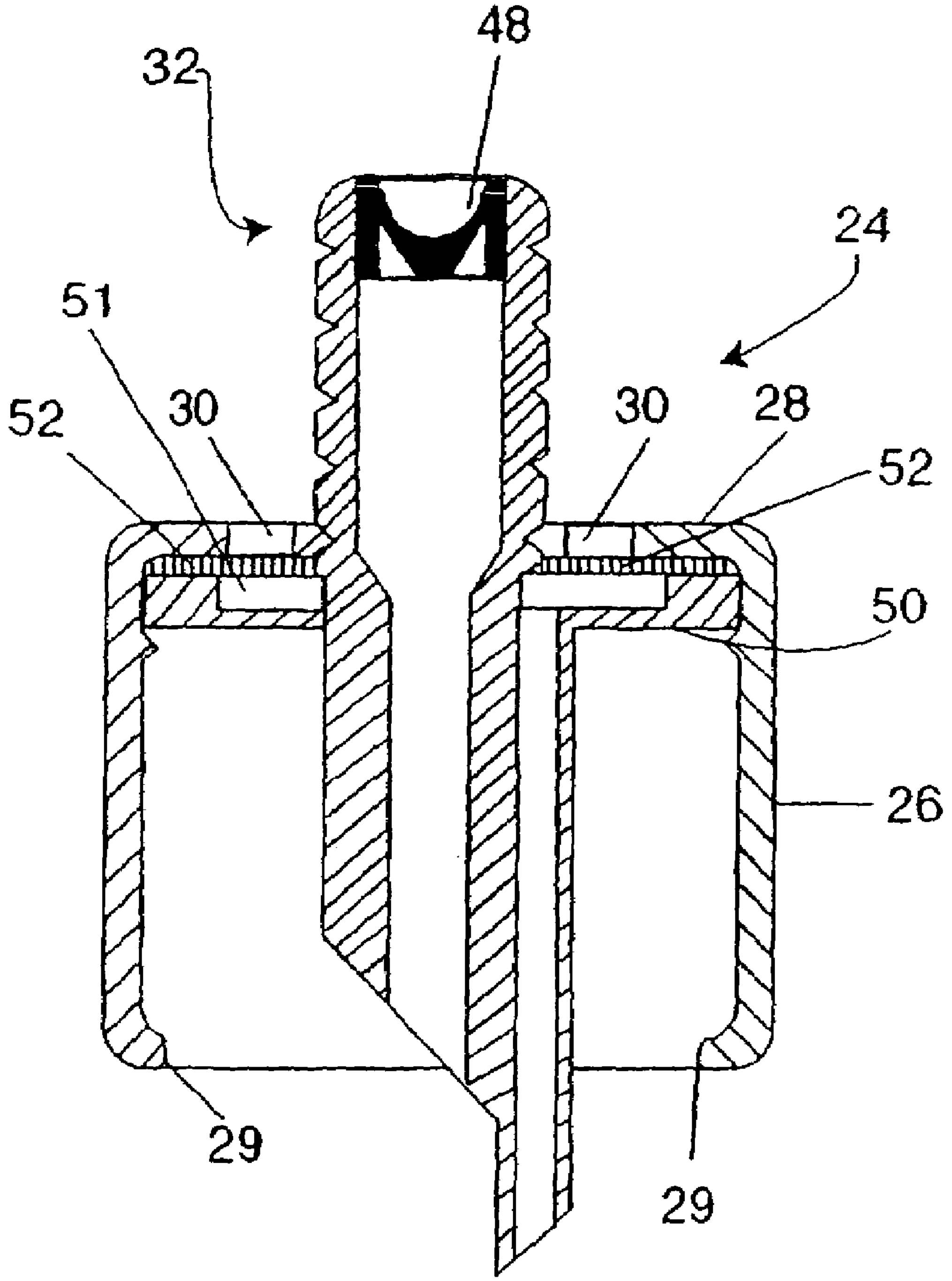
FIG. 5A is a cross-sectional view of the vial access adapter wherein the lower portion of the fluid flow channel had a reduced diameter.

Reference is now made to FIGS. 4 and 5. FIG. 4 shows a top plan view of the vial access adapter and FIG. 5 shows a cross-sectional view of the vial access adapter taken along the line 5—5 of FIG. 4.

In FIG. 4 there are shown: eight vent holes 30 in the flat, horizontal top wall 28, dual spike 34 and 36, and an elastomeric seal 48 positioned inside the threaded luer connector means.

As best seen in FIG. 5, the vial access adapter 24 further comprises an internal second wall 50 which is parallel to the flat, horizontal top wall 28 and is spaced therefrom. Flat, horizontal top wall 28, internal second wall 50, and cylindrical sidewall 26 enclose a chamber 51 therebetween designed to hold a filter 52. The filter is an anti-microbial filter known in the art, such as Whatman Grade HCO1, USP Class 6.

The anti-microbial filter is a circular mat of randomly oriented fibers bound together with a polymeric material, such as a polyester elastomer, ethylene methacrylate, ethylene vinyl acetate, ethylene vinyl alcohol, polyethylene or polypropylene treated with an anti-bacterial agent. The randomly oriented fibers may be made of nylon, cellulose, rayon and polyester.

One of the dual spikes 34 is adapted to carry liquid medicament from vial 10. This spike is integral with the threaded luer connector means 32 and passes through the flat, horizontal top wall 28, and internal second wall 50. When the vial access adapter is assembled with vial 10 and pierces stopper 22, sharp point 38 just clears the bottom surface of stopper 22 to reach the liquid medicament contained in the vial. In use, when the vial is turned upside-down and connected to the vial access adapter, this positioning of the sharp point 38 just below the bottom surface of the stopper allows for maximum amount of withdrawal of medicament from the vial.

The other of the dual spike 36 runs parallel to spike 34, however it only runs from below chamber 51 and is connected to internal second wall 50 and terminates in sharp point 40. It extends into the vial somewhat below sharp point 38 of first spike 34 so that atmospheric air can be introduced into the vial even when the content of the vial is at a minimum volume.

Figure 5B:
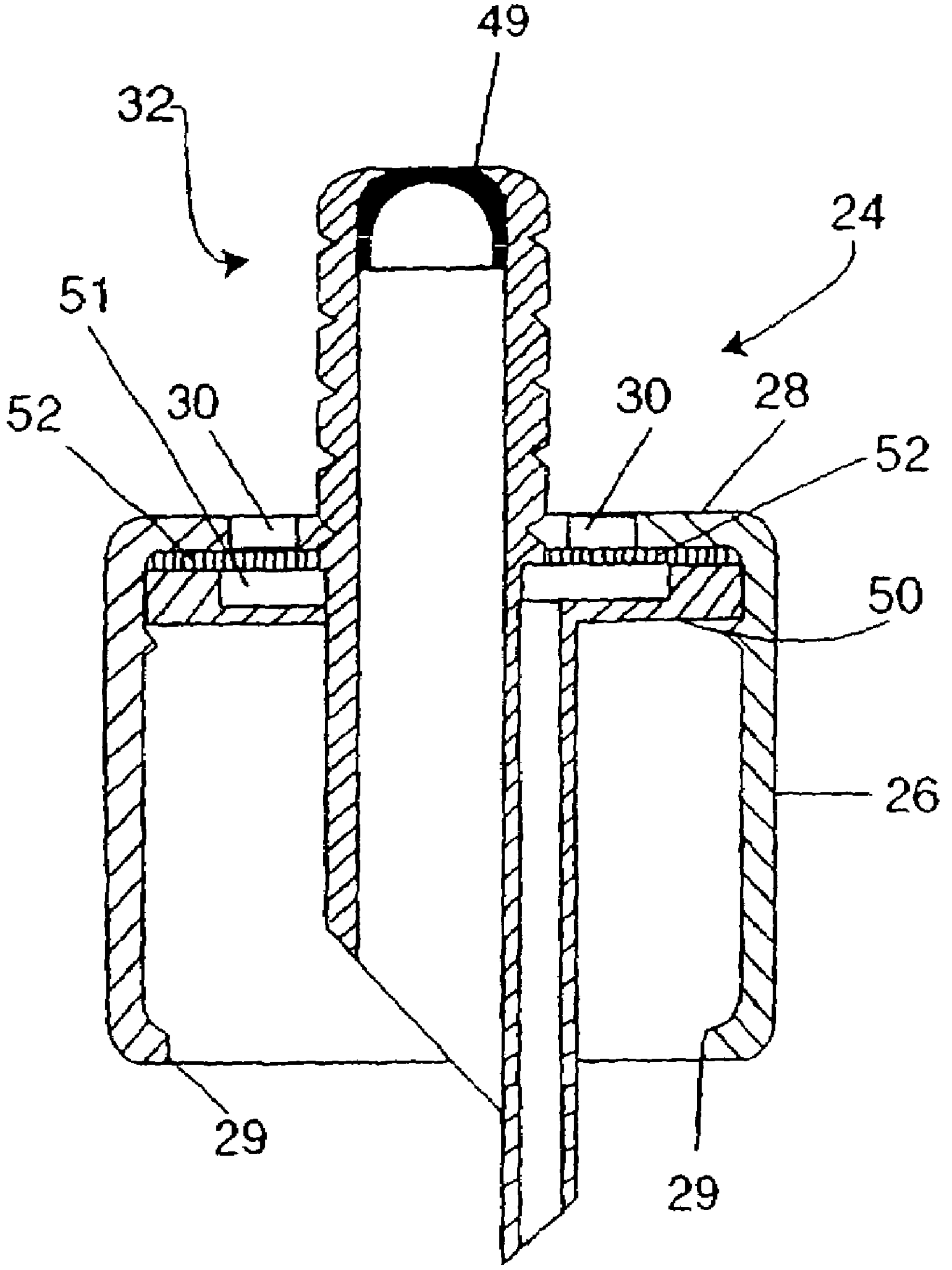
FIG. 5B is a cross-sectional view of the vial access adapter wherein the membrane is of an inverted U-shaped configuration.

The vial access adapter can be used without a seal within the threaded luer connector means 32. Preferably, however, a seal is used to prevent entry of atmospheric air when the vial access adapter is placed on the vial containing a medicament. The seal can be a horizontal, flat elastomeric membrane, or an inverted U-shaped membrane 49 as shown in FIG. 5B, which can be ruptured by a luer connector. Most preferably, the seal is an M-shaped elastomeric seal or membrane capable of resealing itself after one or more puncture by a luer connector.

The M-shaped elastomeric seal or membrane 48 is of inert, gas-impermeable lo polymeric material capable of flexing under pressure. It preferably has a thickness of from about 0.001 mm to about 1.00 mm and a durometer of from about 25 to about 80 Shore A. It is capable of being ruptured by a twisting motion of a luer connector. The configuration of the elastomeric membrane is M-shaped having vertical leg portions and a top surface resembling a cup shape. Suitable elastomeric materials for constructing the diaphragm include:

- natural rubber;
- acrylate-butadiene rubber;
- cis-polybutadiene;
- chlorobutyl rubber;
- chlorinated polyethylene elastomers;
- polyalkylene oxide polymers;
- ethylene vinyl acetate;
- fluorosilicone rubbers;
- hexafluoropropylene-vinylidene fluoride-tetrafluoroethylene terpolymers such as sold under the tradenames of Fluorel and Viton;
- butyl rubbers;
- polyisobutene, such as sold under the tradename Vistanex;
- synthetic polyisoprene rubber;
- silicone rubbers;
- styrene-butadiene rubbers;
- tetrafluoroethylene propylene copolymers; and
- thermoplastic-copolyesters.

Figure 6:
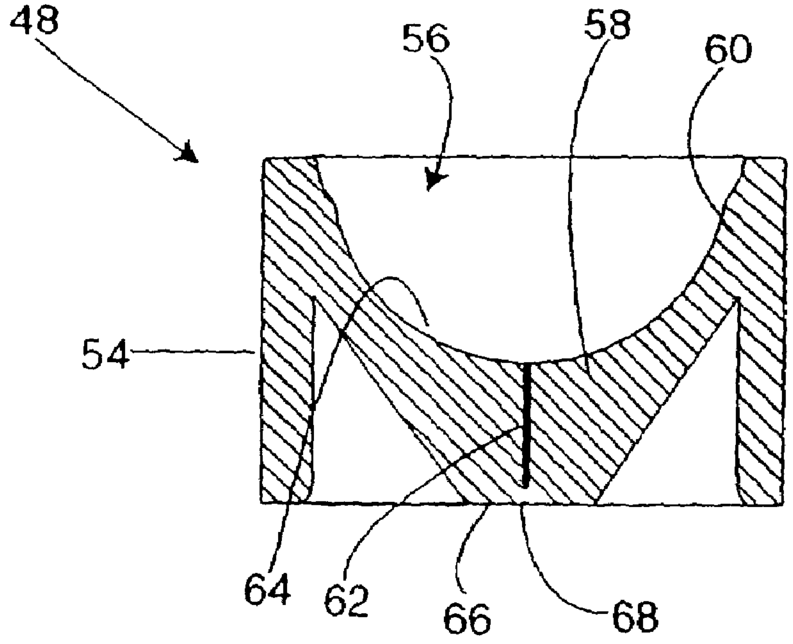
FIG. 6 shows an elastomeric seal in the form of the M-shaped membrane.
Figure 7:
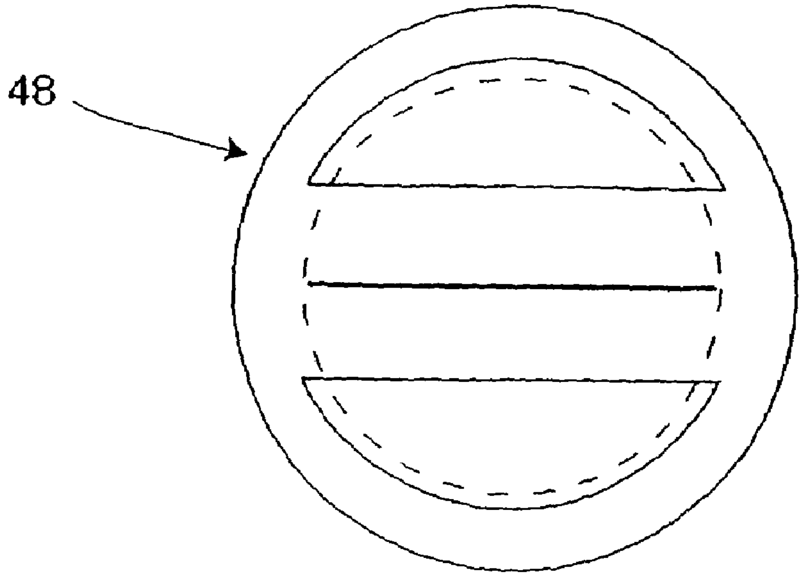
FIG. 7 is a top plan view of the M-shaped membrane shown in FIG. 6.

As best seen in FIGS. 6 and 7, the M-shaped membrane 48 comprises: leg portion 54, and cup-shaped portion 56. Cup-shaped portion comprises: horizontal bottom portion 58; and side portion 60. Leg portion 54 and side portion 60 typically have a thickness of from about 3 to 6 mm while bottom portion 58 typically has a thickness of from about 5 to 20 mm.

The horizontal bottom portion 58 is provided with a slit 62 which extends from the top surface 64 of the horizontal bottom portion toward the bottom surface 66. However, the slit does not penetrate the bottom surface. The unpenetrated membrane, denoted by the numeral 68, has a thickness of from about 0.001 mm to about 2.0 mm. The unpenetrated membrane maintains the content of the container in sealed condition. In use, when this membrane is ruptured by an external access means, such as a luer connector or spike, fluid communication is established between the content of the container and the external access means. Upon disengaging the external access means, the cup-shaped portion of the diaphragm reseals itself for the reason that the membrane is resilient and springs back to its original configuration. As a result, the container is resealed until the fluid withdrawal process is repeated.

The M-shaped membrane is bounded to the medicament-carrying spike 34 at its opening thereof by conventional means known in the art.

Figure 8:
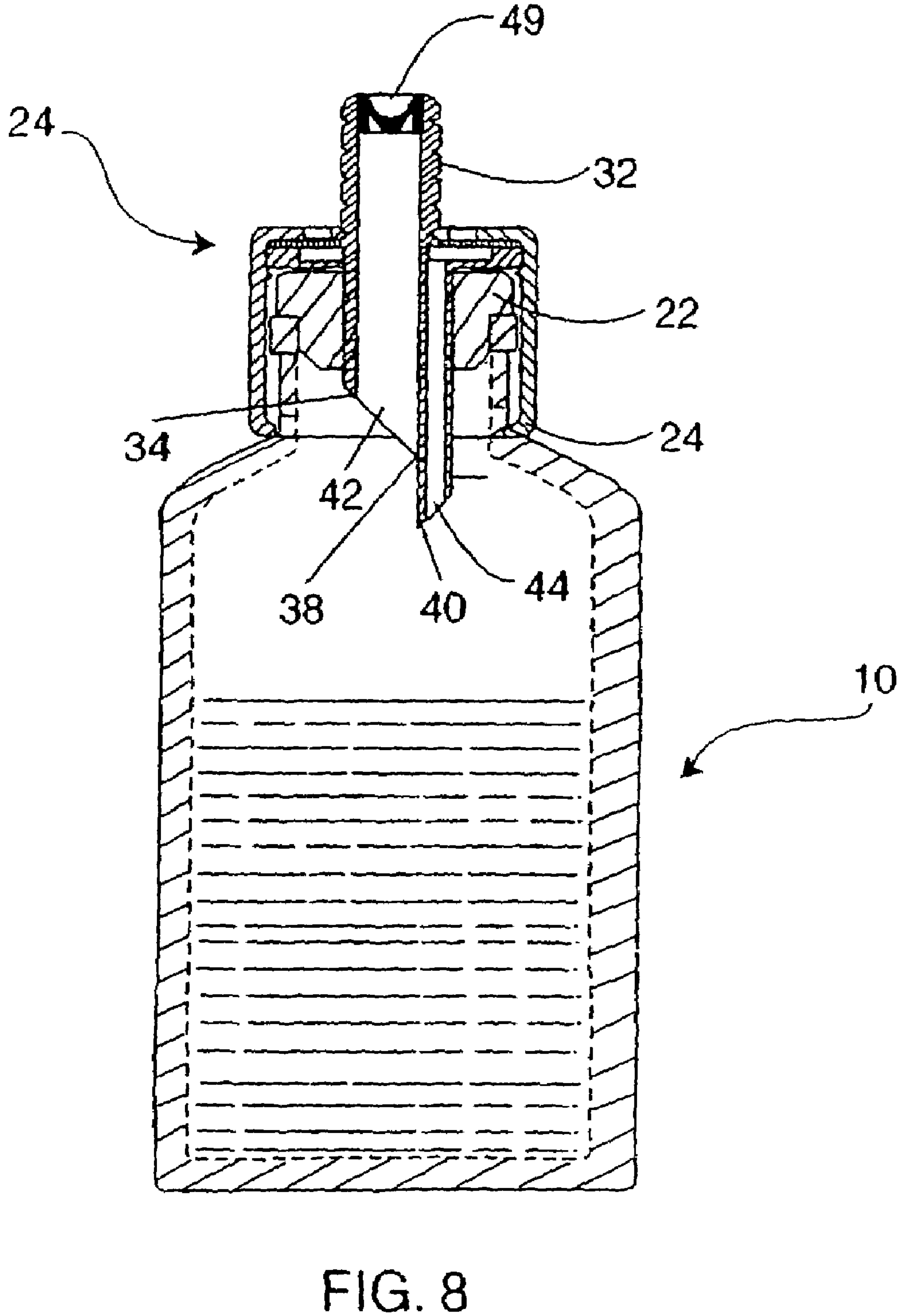
FIG. 8 shows the vial access adapter assembled with the vial.

FIG. 8 shows in cross-sectional view the vial access adapter 24 and the vial 10 assembly. Dual spikes 34 and 36 have been inserted into the vial through stopper 22. Liquid medicament passage 42 just clears the bottom portion of the stopper so that, when the assembly is turned upside-down, essentially all the liquid medicament may be withdrawn from the vial.

Spike 36 having air-flow passage 44 therein is longer than spike 34 having liquid medicament flow passage 42 therein in order to prevent air from circulating back into the liquid medicament flow passage during withdrawal of the liquid medicament from the vial.

Figure 9:
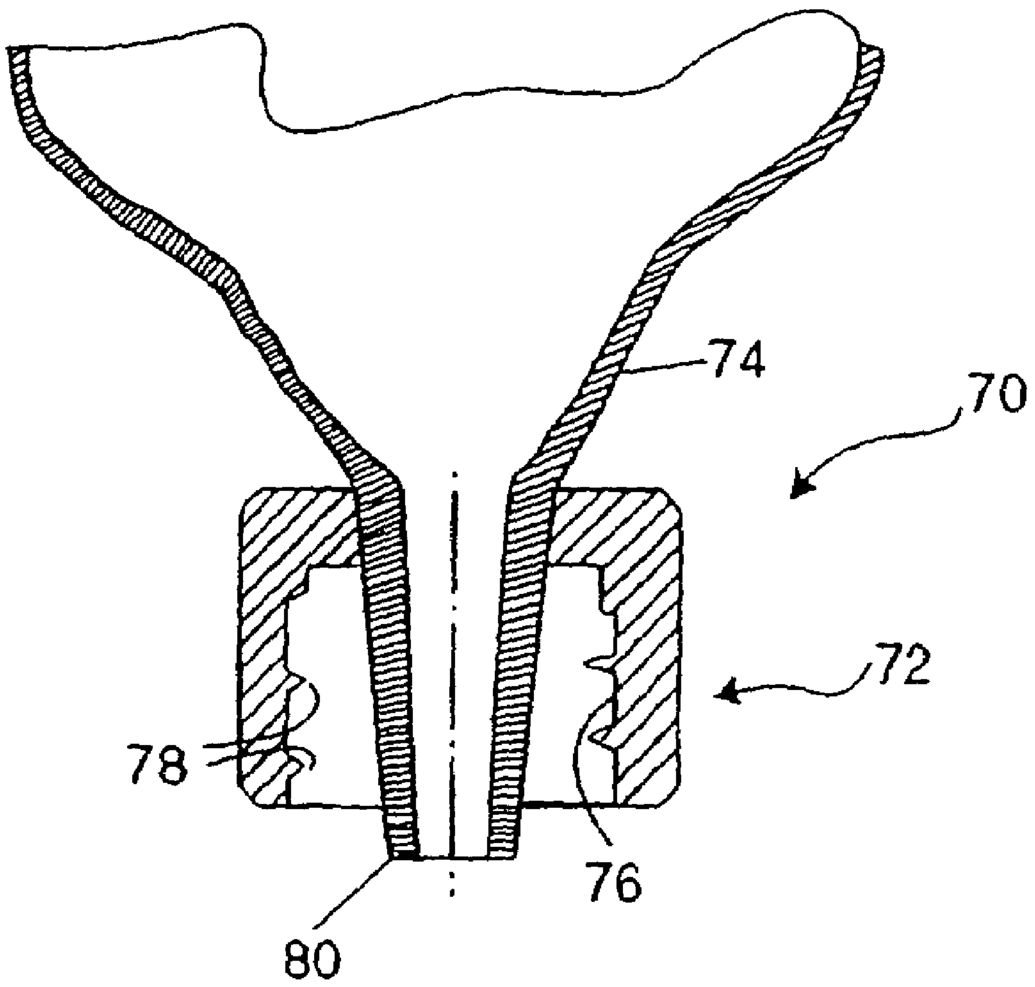
FIG. 9 illustrates a luer connector attachable to the vial access adapter.

FIG. 9 shows in cross-sectional view a typical luer connector 70 attachable to the vial access adapter of the present invention. The luer connector comprises a cylindrical cap 72 and a tubing conduit 74. Cylindrical cap 72 comprises inside wall 76 having threads 78 therein extending towards tubing conduit 74. Upon attachment, luer connector 70 will engage thread means 32 of vial access adapter 24. Tubing conduit 74 has a bottom portion 80 which extends beyond the cylindrical cap and is adapted to rupture the elastomeric membrane 48 or 49 of the vial access adapter 24.

Figure 10:
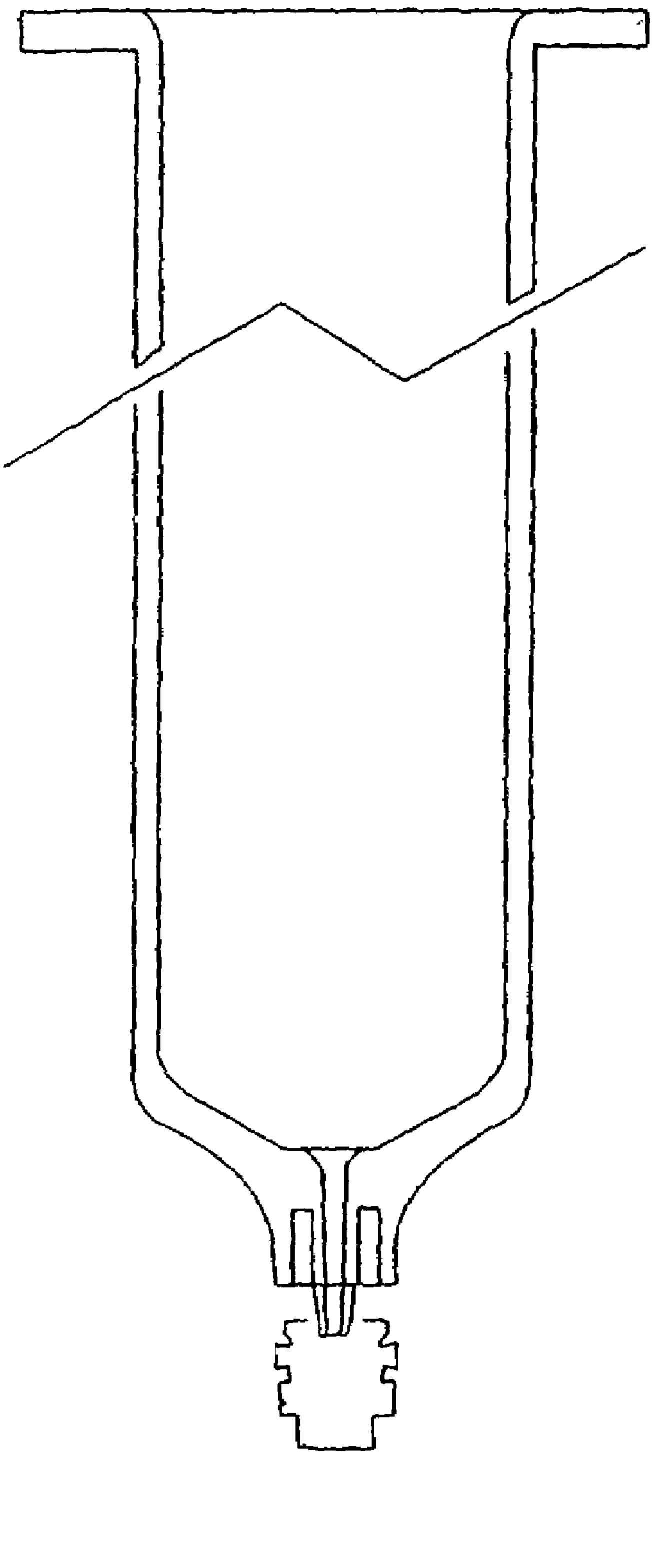
FIG. 10 illustrates, in a cross-sectional view, a portion of the threaded luer connector prior to penetration of a membrane by the luer connector of a syringe.

FIG. 10 shows in cross-sectional view a portion of the threaded luer connector means with the elastomeric membrane therein prior to penetration of the membrane by the luer connector of a syringe.

Figure 11:
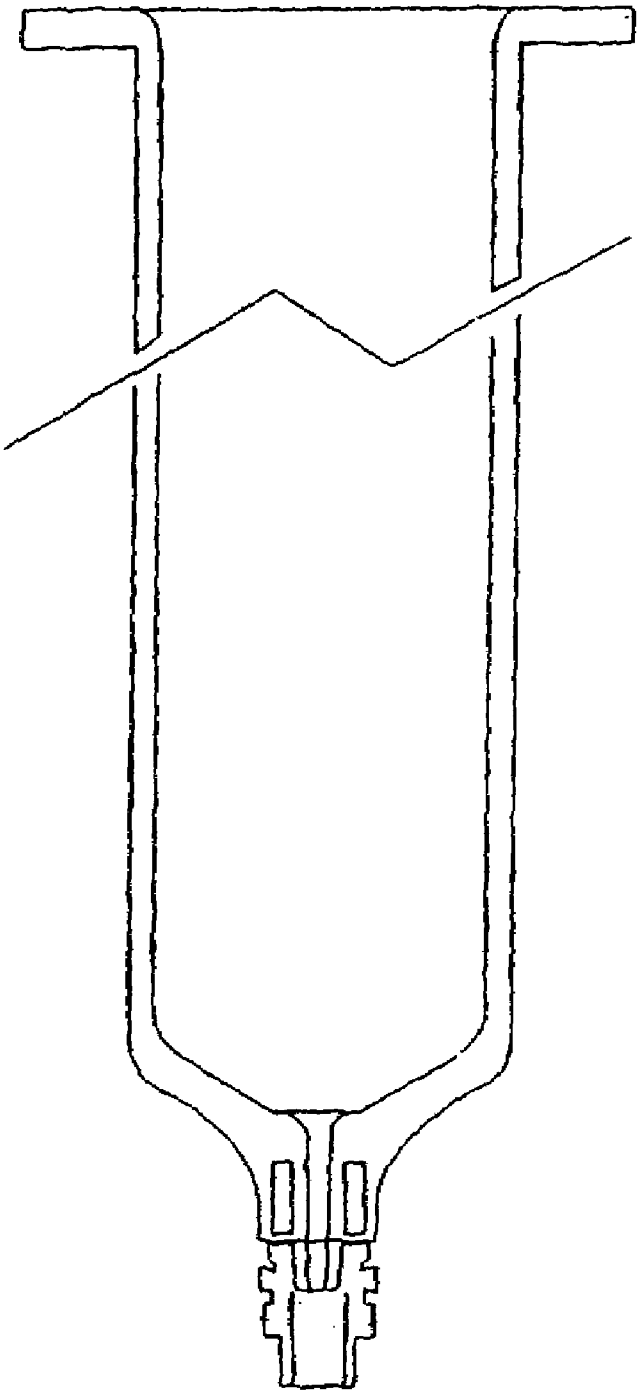
FIG. 11 illustrates, in a cross-sectional view, a portion of the threaded luer connector during penetration and breakthrough of the membrane by the luer connector of the syringe.

FIG. 11 shows in cross-sectional view a portion of the threaded luer connector means with the elastomeric membrane therein during penetration and break-through of the membrane by the luer connector of a syringe.

In use, the vial access adapter of the first embodiment is engaged with a vial containing a liquid medicament therein by a snap-on motion. The dual spike penetrates the stopper establishing fluid communication between the vial and the vial access adapter. Next, an external connector or the luer connector of a syringe is engaged with the vial access adapter by a twisting motion, threading the luer connector into the luer connector means of the vial access adapter. Upon sufficient twisting the elastomeric membrane is ruptured and fluid communication is achieved between the luer connector and the vial access adapter. These steps of engagement are accomplished while the vial containing the liquid medicament is positioned on a flat surface in a right-side-up position. Upon completing these steps, the vial is turned upside-down and the liquid medicament is transferred from the vial into the external luer connector having tubing conduit therein from which the medicament is administered to a patient. When a syringe, having a plunger therein equipped with a luer connector is used, withdrawal of the liquid medicament is accomplished by moving the plunger towards its open end and thereby drawing the liquid medicament into the syringe barrel. The desired amount of liquid medicament withdrawn can be seen in the syringe. Upon disconnecting the external luer connector from the vial access adapter, the M-shaped elastomeric membrane reseals itself thereby keeping the liquid medicament in the vial in aseptic condition. The self-sealing membrane allows repeated access to the liquid medicament contained in the vial.

A second embodiment of the present invention is shown in FIGS. 12, 13, 14, 15, 16, 17 and 18 wherein the numerals marked by prime (') denote like elements described in the first embodiment.

Figure 12:
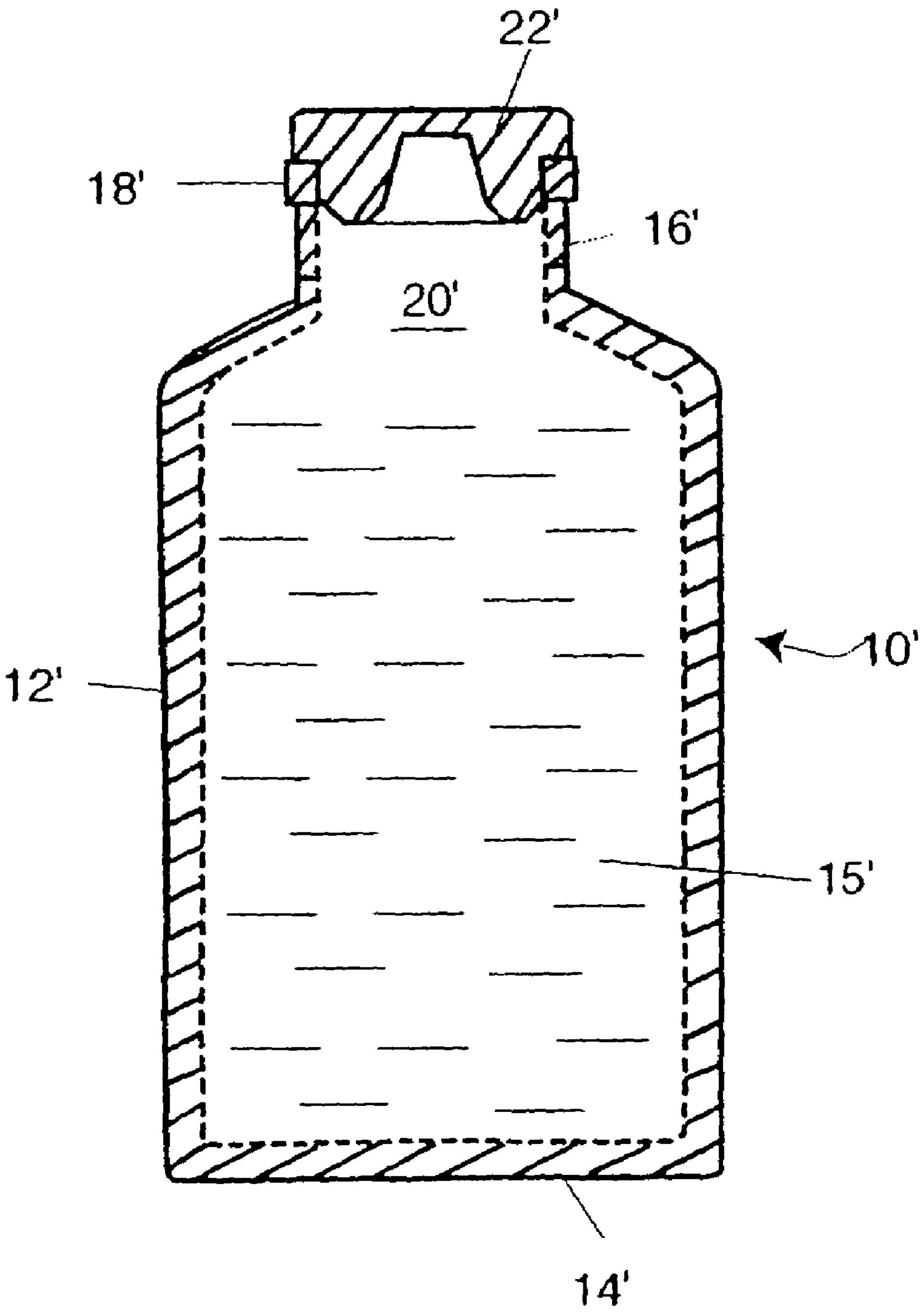
FIG. 12 is a cross-sectional view of a typical vial containing a medical fluid therein, used in combination with the second embodiment of the vial access adapter of the present invention.

FIG. 12 shows the cross-section of vial 10' in an upright position having a medical fluid 15' therein comprising: a cylindrical side wall 12', a flat bottom portion 14', and a constricted neck portion 16' terminating in a rim 18'. The neck portion and rim define an open area 20 closed by elastomeric stopper 22' hermetically sealing the medical fluid 15' contained in the vial. The vial typically contains of from about 5 ml to about 150 ml or more of the medical fluid.

Figure 13:
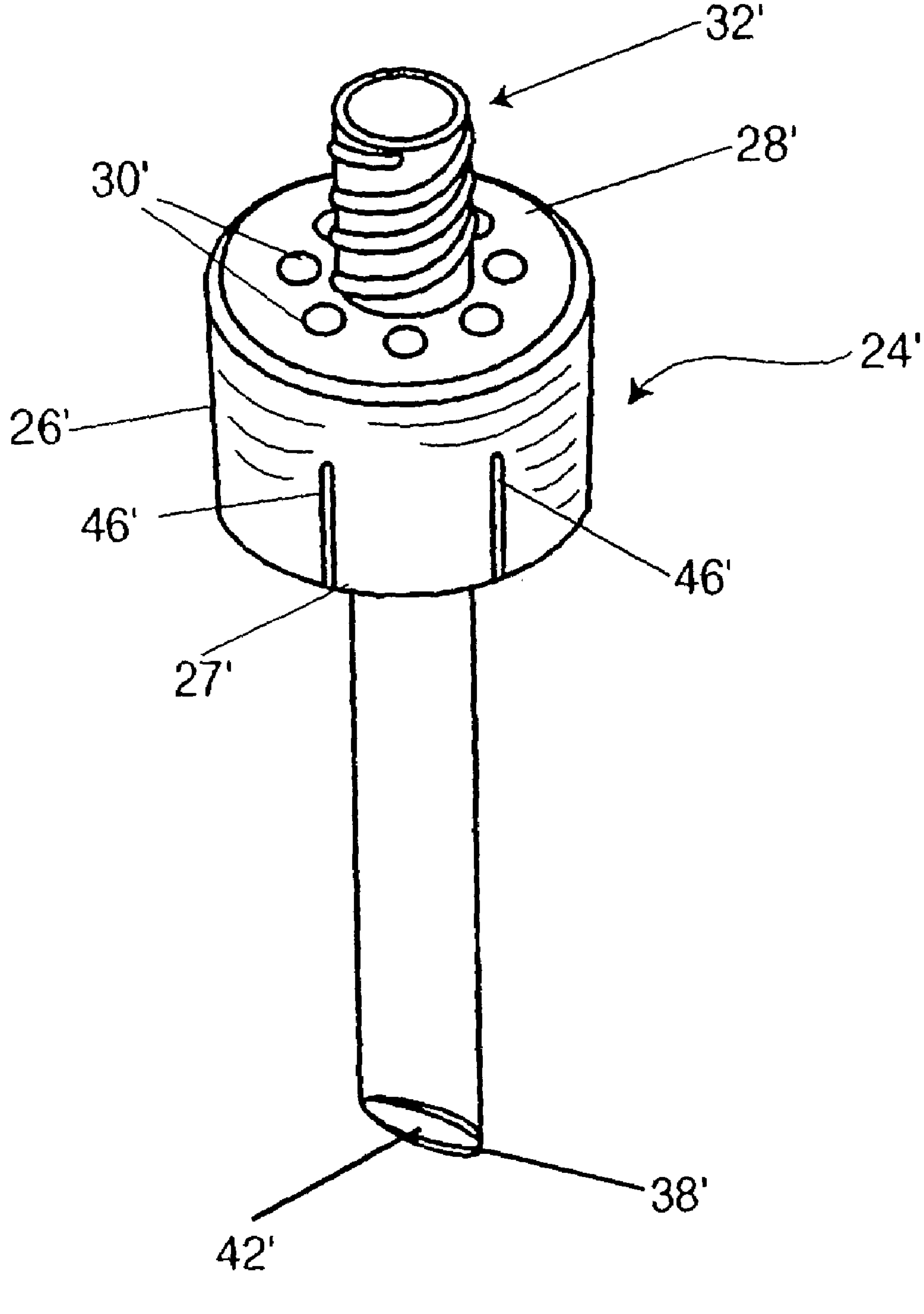
FIG. 13 is a perspective view of the vial access adapter showing the cylindrical side wall, flat top portion with vent holes, and threaded luer connector means rising above the flat top portion.
Figure 14:
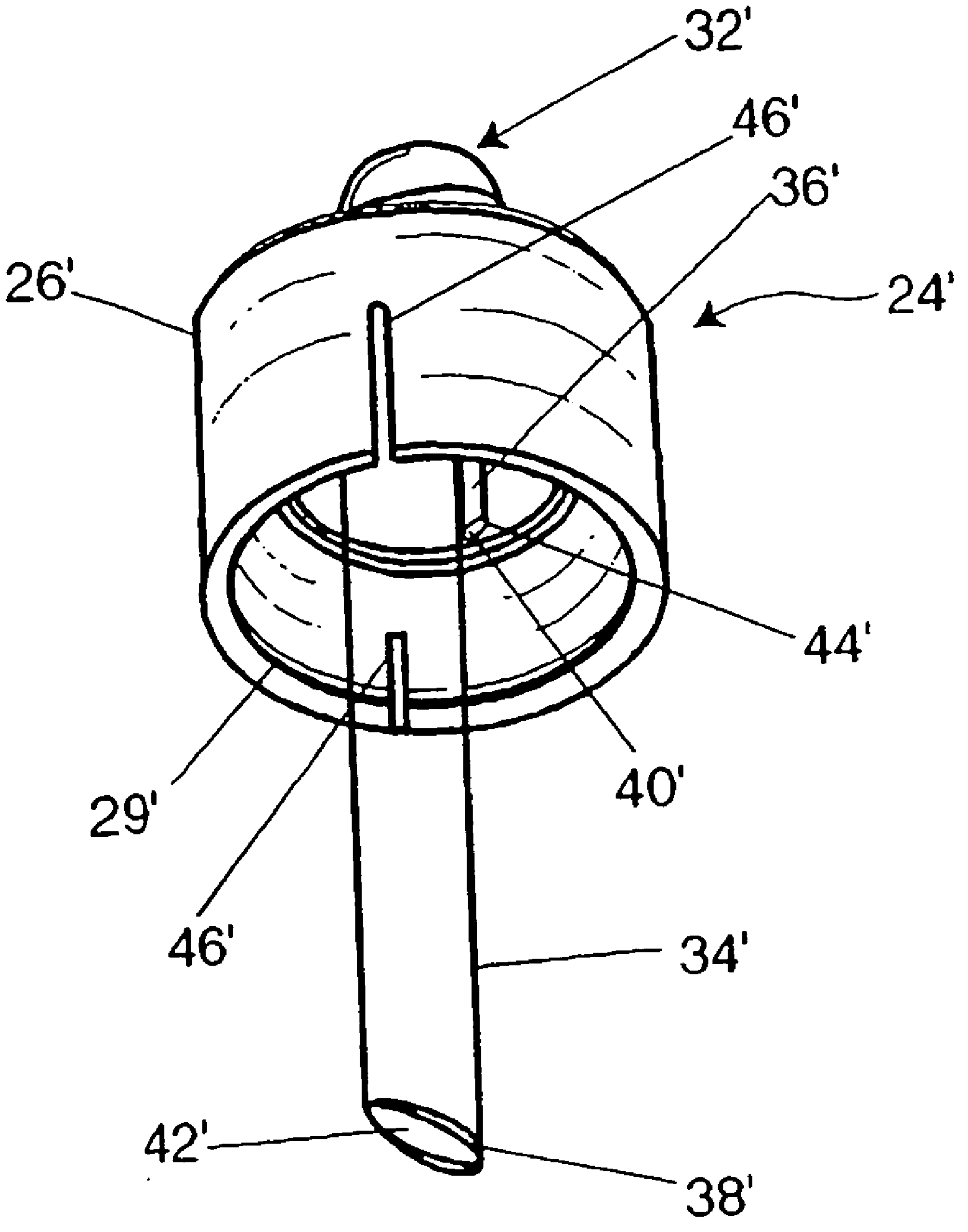
FIG. 14 is a another perspective view of the vial access adapter showing the cylindrical side wall, the medical fluid spike, and the air passage spike.
Figure 18:
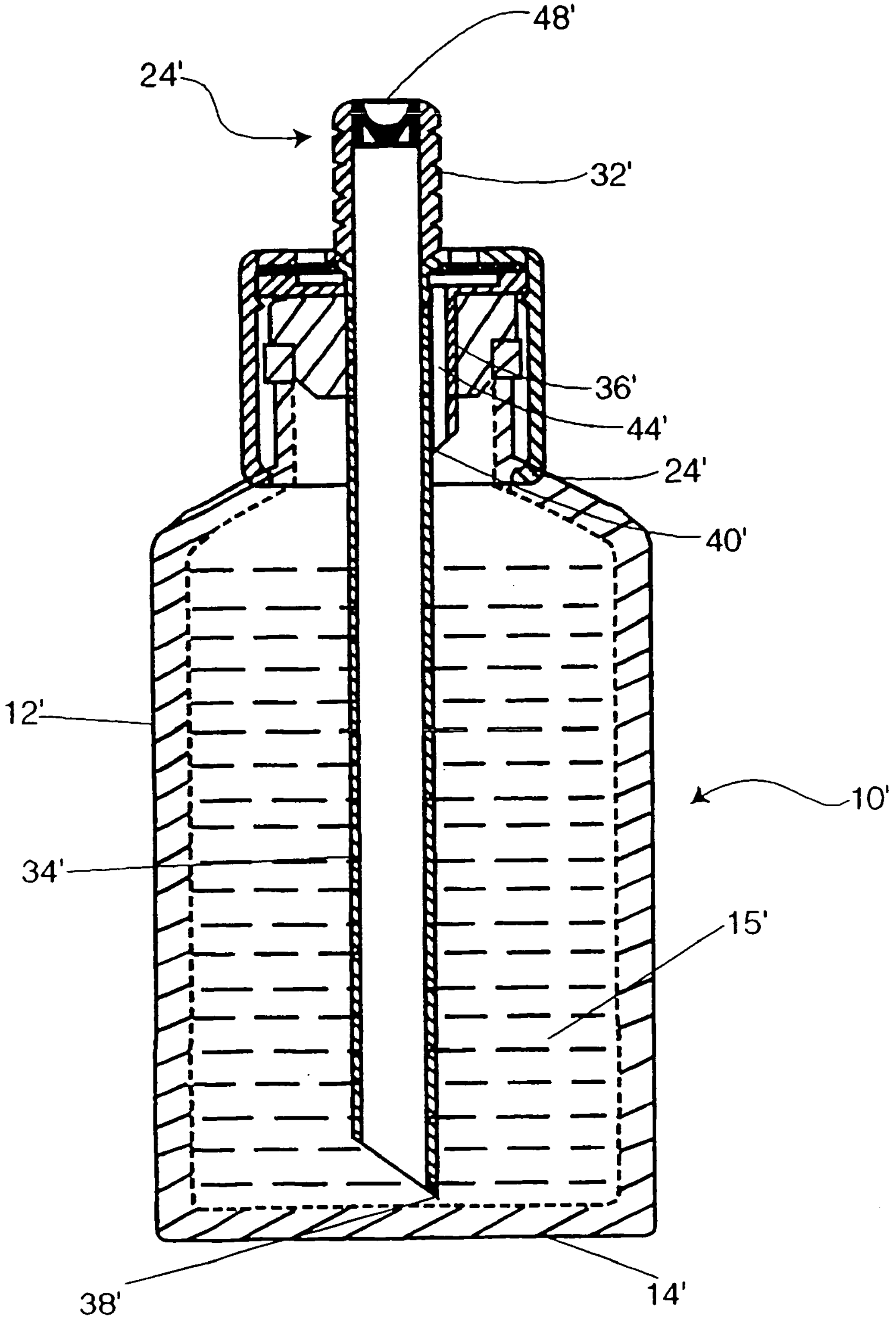
FIG. 18 shows the vial access adapter assembled with the vial.
Figure 19:
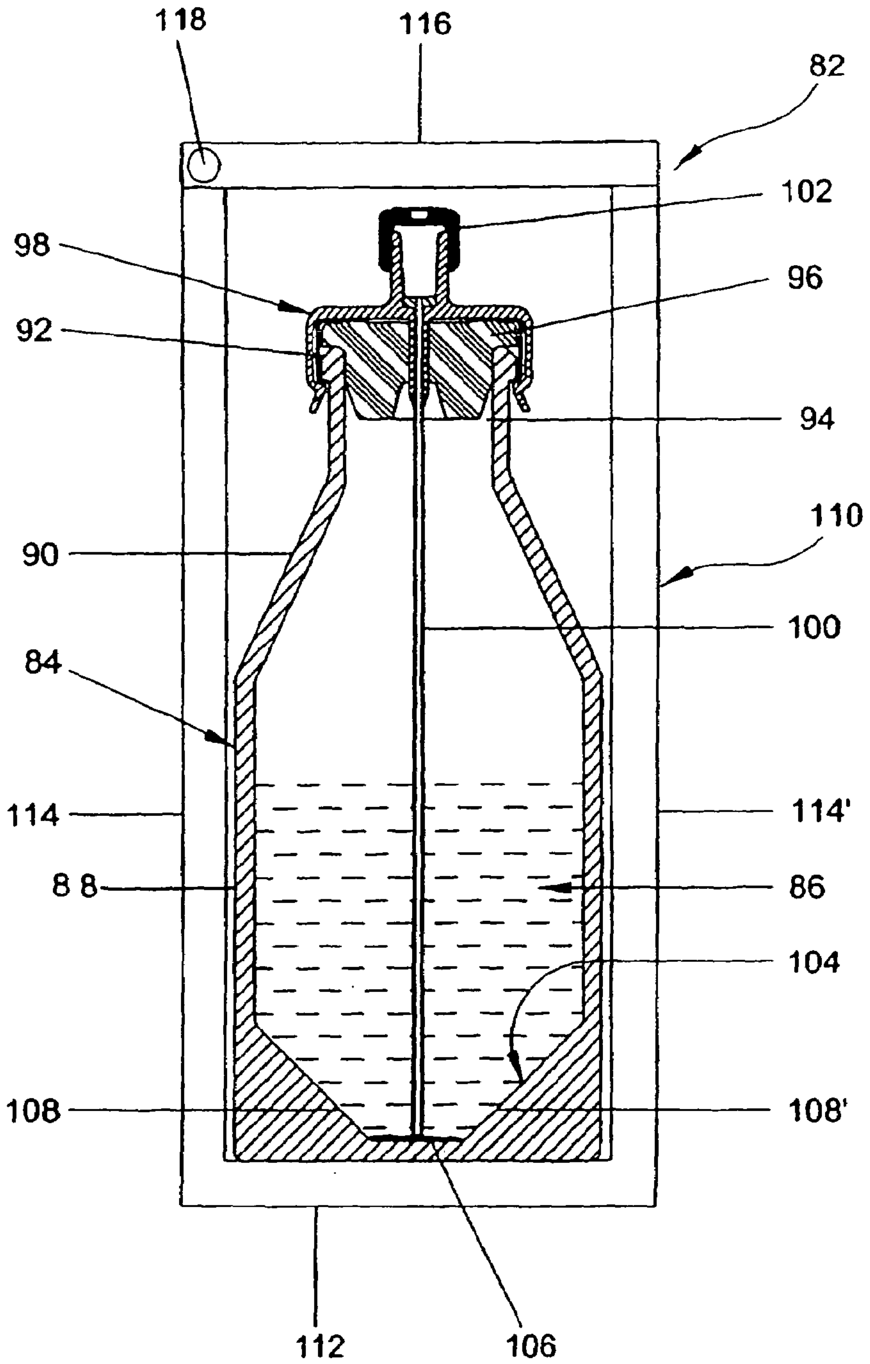
FIG. 19 is a cross-sectional view of a vial having a V-shaped bottom shrouded in a heavy protective container illustrating the third embodiment of the present invention.

The vial access adapter, generally designated by the numeral 24' and shown in perspective views in FIGS. 13 and 14, comprises:

a cylindrical side wall 26' terminating in a rim 27'; a flat horizontal top wall 28' having vent holes 30' therein; threaded luer connector means 32' projecting vertically above the horizontal top wall 28'; and dual spike 34' and 36', terminating in sharp points 38' and 40', extending parallel to each other, and having flow passages therein 42' and 44', one being designed for passage of a fluid medicament, and the other being designed for passage of air. Spike 34' is elongated to reach bottom portion 14' of vial 10' as shown in FIG. 18. Spike 36' is short and extends just below the bottom surface of elastomeric stopper 22'. Cylindrical side wall 26' of the vial access adapter 24' is preferably provided with a plurality of slots 46' to facilitate the positioning of the vial access adapter onto vial 10' by a snap-on motion. In order to securely hold the vial access adapter on the vial, rim 27' of cylindrical side wall 26' is equipped with protuberance 29' projecting inward towards dual spike 24' and 36'. Protuberance 29' engages the neck portion 16' just below the rim portion 18' of vial 10'.

Figure 15:
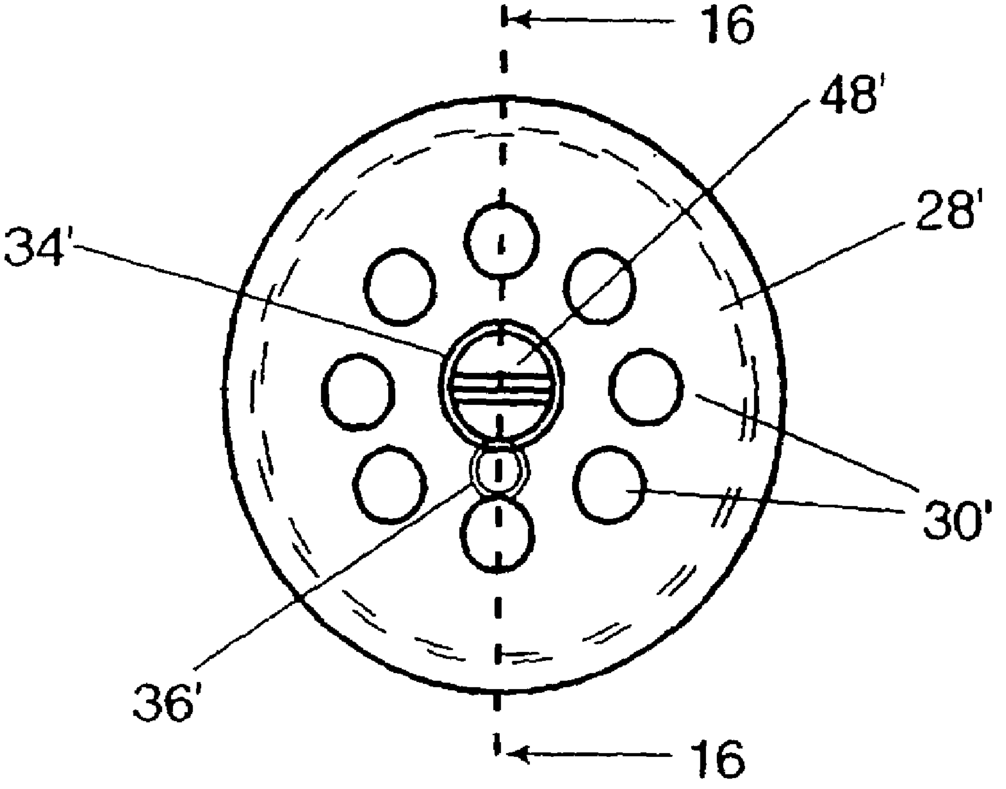
FIG. 15 is a top plan view of the vial access adapter.
Figure 16:
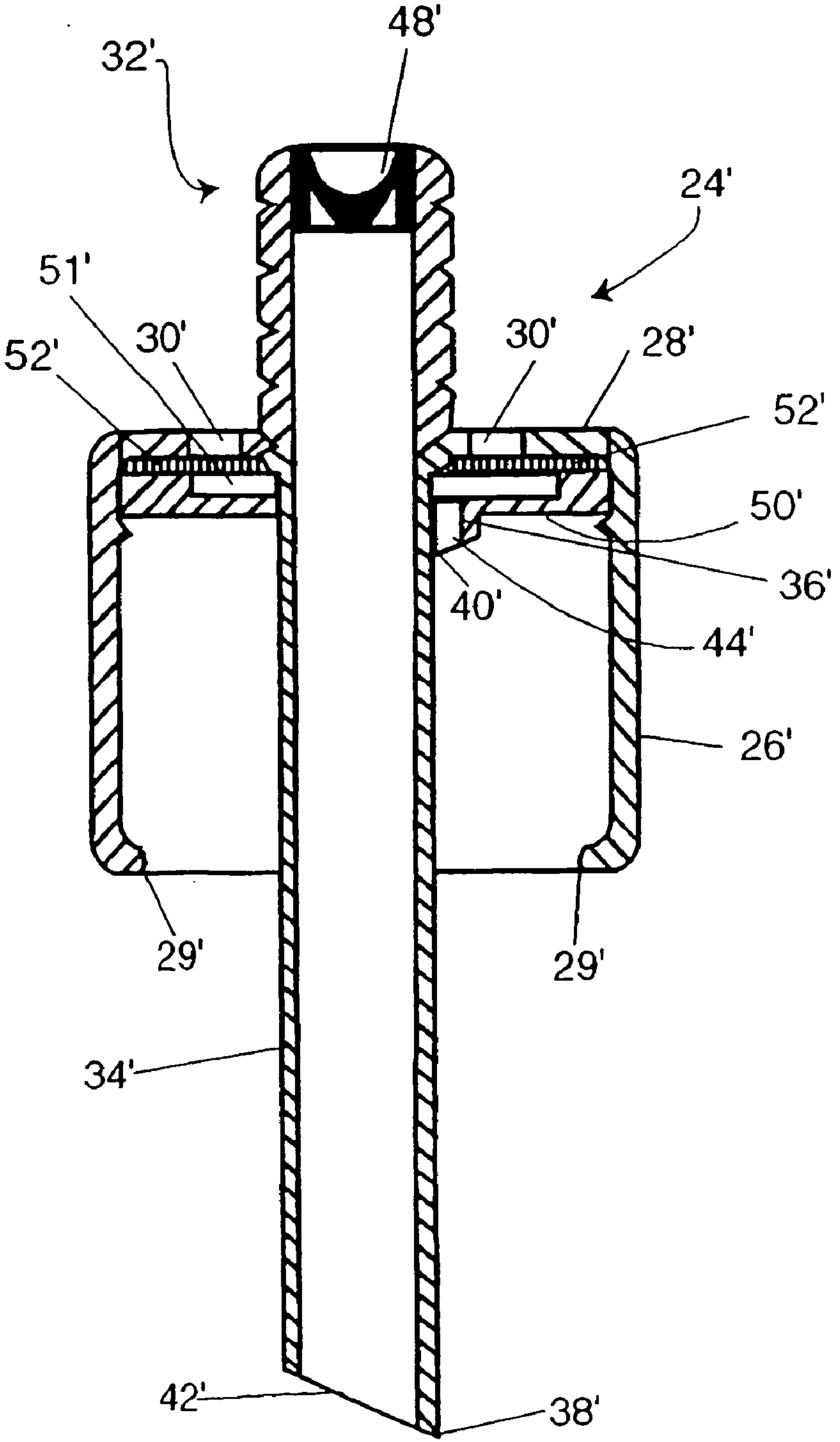
FIG. 16 is a cross-sectional view of the vial access adapter, having an M-shaped membrane therein, taken along the line 16—16 of FIG. 15.
Figure 17:
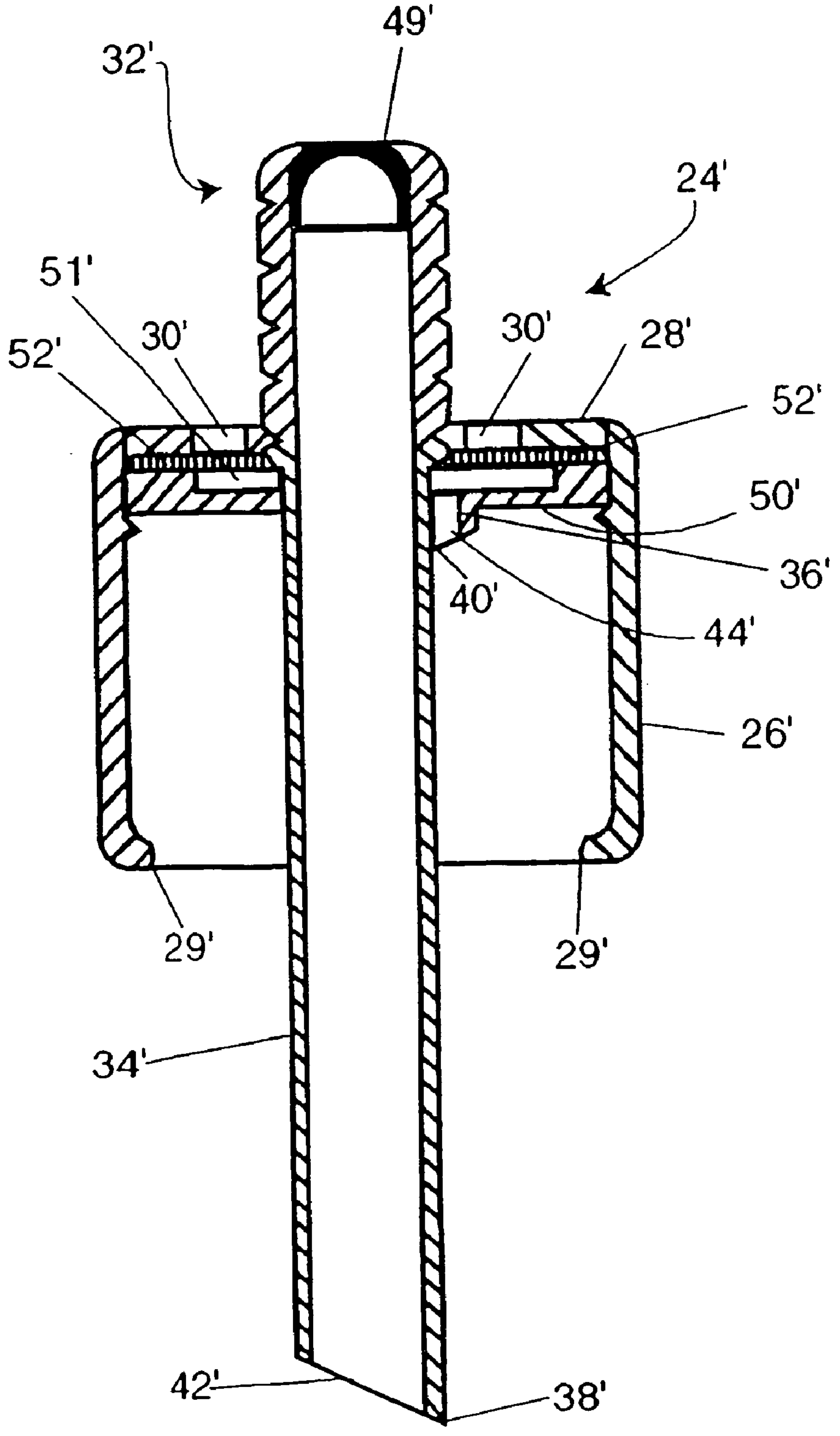
FIG. 17 is a cross-sectional view of the vial access adapter wherein the membrane is of an inverted U-shaped configuration.

Reference is now made to FIGS. 15, 16, 17 and 18. FIG. 15 shows a top plan view of the vial access adapter, and FIG. 16 shows a cross-sectional view of the vial access adapter taken along the line 16—16 of FIG. 15. In FIG. 15 there are shown: eight vent holes 30' in the flat, horizontal top wall 28', dual spike 34' and 36', and an elastomeric seal 48' positioned inside the threaded luer connector means.

The vial access adapter 24' further comprises an internal second wall 50' which is parallel to the flat, horizontal top wall 28' and is spaced therefrom. Flat, horizontal top wall 28', internal second wall 50', and cylindrical side wall 26' enclose a chamber 51' therebetween designed to hold a filter 52'. The filter is an anti-microbial filter known in the art, such as Whatman Grade HCO1, USP Class 6.

In use, the vial access adapter of the second embodiment is engaged with the vial containing a liquid medicament therein by a snap-on motion. The dual spike penetrates the stopper establishing fluid communication between the vial and the vial access adapter. Next, an external connector or the luer connector of a syringe is engaged with the vial access adapter by a twisting motion, threading the luer connector into the luer connector means of the vial access adapter. Upon sufficient twisting the elastomeric membrane is ruptured and fluid communication is achieved between the luer connector and the vial access adapter. These steps of engagement are accomplished while the vial containing the liquid medicament is positioned on a flat surface in a right-side-up position. Upon completing these steps, the liquid medicament is transferred from the vial into the external luer connector having tubing conduit therein from which the medicament is administered to a patient. When a syringe, having a plunger therein equipped with a luer connector is used, withdrawal of the liquid medicament is accomplished by moving the plunger towards its open end and thereby drawing the liquid medicament into the syringe barrel. The desired amount of liquid medicament withdrawn can be seen in the syringe. Upon disconnecting the external luer connector from the vial access adapter, the M-shaped elastomeric membrane reseals itself thereby keeping the liquid medicament in the vial in aseptic condition. The self-sealing membrane allows repeated access to the liquid medicament contained in the vial.

The vial access adapter body of both these embodiments is made of rigid or semi-rigid polymeric materials and can be used on bottles and vials made of glass or rigid or semi-rigid polymeric materials. The liquid medicament contained in the bottles and vials can be a therapeutic, a diagnostic, or a nutritional preparation.

A third embodiment of the present invention is specifically directed to a vial enshrouded in a protective cover to prevent radiation emission from a nuclear product contained in a vial. In general, however, the configuration of the vial allows delivery of its content of other medicines to withdraw close to all the medicine contained in the vial which is in a right-side-up position on a horizontal surface.

Reference is now made to a third embodiment of the present invention.

FIG. 9 is a cross-sectional view of a vial in a protecting container, often referred to as PIG, which is typically made of lead in order to shield the environment from a nuclear product contained in the vial. The vial and protective container are generally designated by the numeral 82. The vial 84 is in an upright position having a nuclear medicine 86 therein comprising: a cylindrical side wall 88; a constricted neck portion 90 terminating in a rim 92; open area 94 defined by constricted neck portion and rim is closed by an elastomeric stopper 96, which hermetically seals the nuclear medicine 86 contained in the vial; an integral skirt and luer connector designated at 98; a fluid removal tube 100 extending towards the bottom of the vial; a luer cap 102 covering the opening in the luer connector; and a V-shaped bottom generally designed at 104 having a horizontal bottom portion 106, and side portions 108 and 108' constituting the side portions thereof. The horizontal bottom portion may terminate in a sharp angle, or it may extend as a horizontal surface defining obtuse angles with side portions 108 and 108' as illustrated in the drawing. The fluid removal tube 100 is precisely designed to reach horizontal bottom portion 106 in order to completely or almost completely remove the liquid from the vial.

The protective container generally designated at 110, enshrouds the vial and comprises:

a horizontal bottom wall 112;

vertical side walls 114 and 114'; and top wall or cover 116 which is openable with a hingel 18 or other means The vial snuggly fits into the protective container the content of which may be reached by opening the top wall of the protective container.

Figure 20:
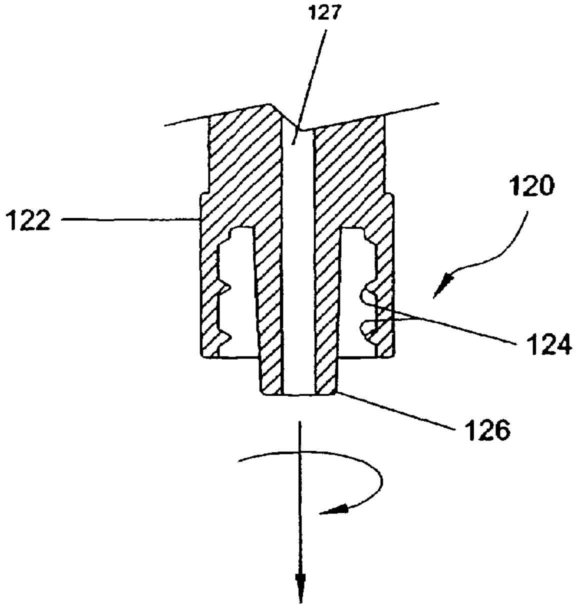
FIG. 20 is a partial cross-sectional view of the male portion of a vial access adapter.

FIG. 20 is a partial cross-sectional view on an enlarged scale of the male portion, generally designated at 120, of the luer connecting device wherein: the numeral 122 refers to the outside wall; the numeral 124 denotes threads on the inside wall; and the numeral 126 denotes the tube of the male portion with a longitudinal channel 127 therein. The male portion is to engage to female luer fitting which is shown in FIG. 21.

Figure 21:
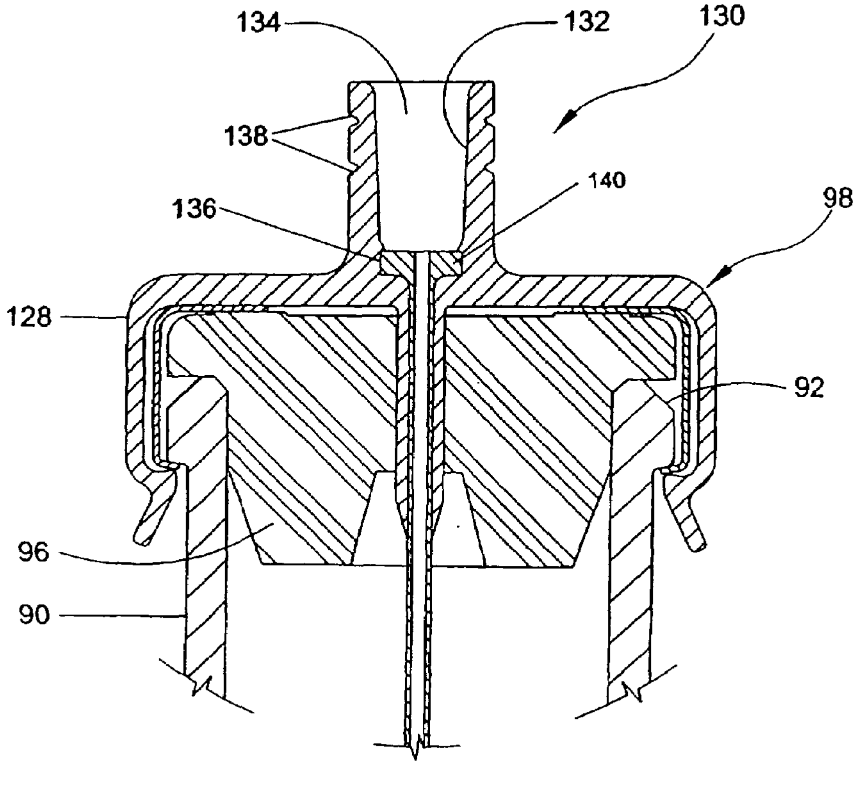
FIG. 21 is a partial cross-sectional view of the vial having a V-shaped bottom and the female portion of the non-vented vial access adapter.

FIG. 21 is a partial cross-sectional view of the V-shaped vial 84 having: a constricted neck portion 90; a rim portion 92; and an elastomeric stopper 96 closing the open area of the vial. The rim and the elastomeric stopper held within the rim is further closed by a female luer connector, generally designated by the numeral 98 which comprises:

A skirt 128 having a robust fit with rim 92; which fit prevents the skirt from rotation when the male portion 120 of the luer connecting device is attached to the luer female fitting, generally designated at 130.

The skirt 128 is integral with the luer female fitting 130 which fitting comprises an inside wall 132 defining a channel 134 therein serving as a fluid pathway when male portion 120 of the luer connecting device is mated with the luer female fitting 130; groove in the bottom portion of the female luer connector; and an outside wall having the male portion 120 of the luer connecting device. Once the skirt has been mapped on the rim of the vial, the fluid removal tube 100 is inserted through the channel 134 through the top of the female luer connector. The fluid removal tube 100 comprises: a wide top portion 140 which slideably fits into grooves 136 without closing the channel 134 in tube 100 which extends to the V-shaped bottom portion 104 in vial 84.

The action of mating the male luer connector 120 with the female luer connector 130 causes the fluid removal tube 100 to snap into groove 136 in the bottom portion of channel 134. This results in a fluid tight seal between the fluid removal tube and channel 134.

Figure 22:
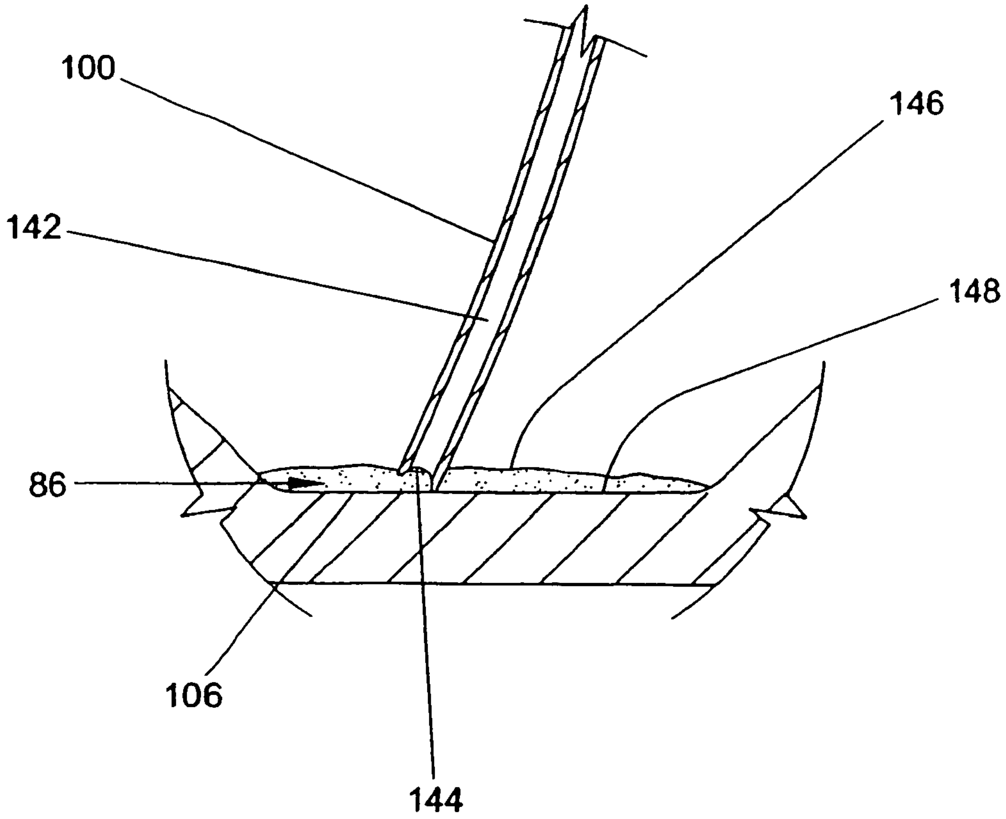
FIG. 22 is a partial cross-sectional view of the bottom of the V-shaped vial containing a small portion of a medical fluid.

FIG. 22 is a partial cross-sectional view of the bottom of vial 84 and the medicinal fluid 86 contained in the bottom of the vial, wherein:

the numeral 100 denotes the fluid withdrawal tube having a fluid pathway 142 therein;

the numeral 86 denotes the medicinal fluid having a top surface 146 and a bottom surface 148;

the numeral 106 denotes the horizontal bottom portion of the vial; and the numeral 144 denotes the terminating profile of the fluid withdrawal tube 100.

The fluid removal tube must have a length top reach and have close contact with the bottom portion of the vial in order to remove most of the medicinal fluid therein. The tube is made of flexible polymeric material able to flex to the side as illustrated in FIG. 22. The configuration of the tube is cylindrical having a circular or oval cross-sectional configuration. Upon flexing, one portion of the terminating end rubs against the horizontal bottom portion 106 of the vial, and the bottom surface 148 of the medicinal fluid, while another portion of the terminating end at least reaches the top surface 146 of the medicinal fluid.

Figure 23:
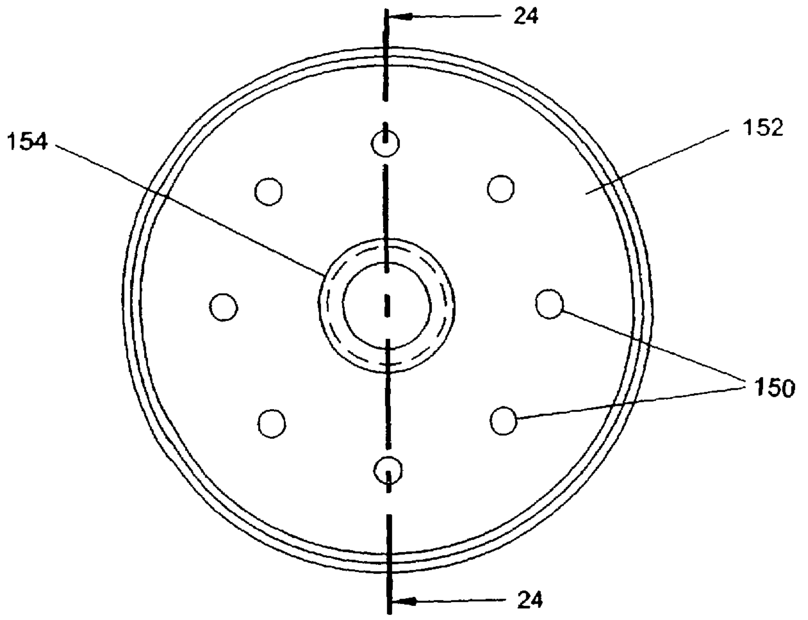
FIG. 23 shows a top plan view of the V-shaped vial equipped with the female portion of the vented vial access adapter.
Figure 24:
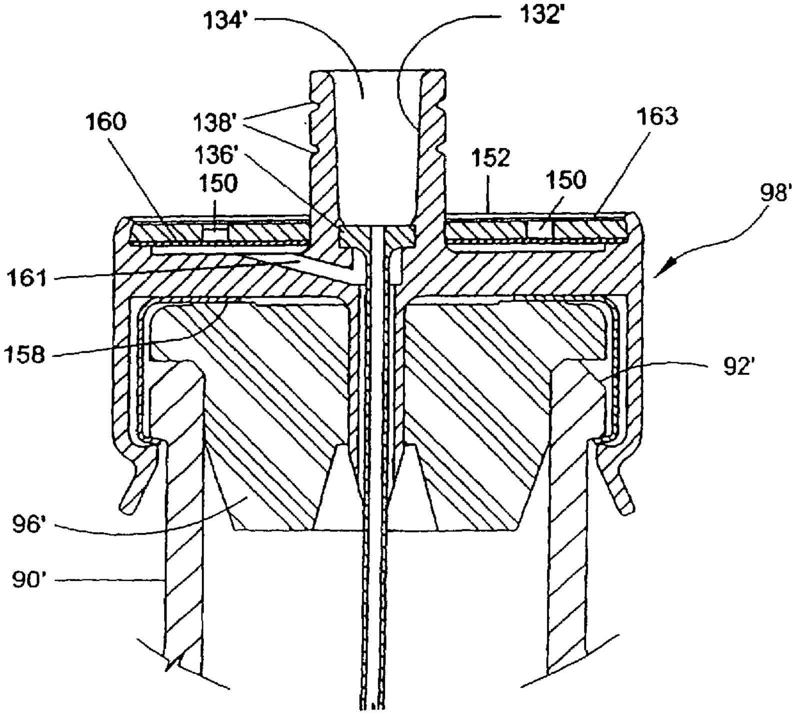
FIG. 24 is a partial cross-sectional view of the V-shaped vial equipped with the female portion of the vial access adapter taken along the line 24—24 of FIG. 23.

FIGS. 19–22 show a non-vented embodiment of the present invention while FIGS. 23–24 show a vented embodiment thereof. FIG. 23 shows a top plan view of the table top dispensing vented vial access adapter, and FIG. 24 shows a partial cross-sectional view thereof taken along the line 24—24 of FIG. 23. In FIG. 23 there are shown eight vent holes 150 in the flat, horizontal top wall 152, and fluid removal tube 154.

In this vented embodiment of the present invention the tabletop dispensing vial access adapter further comprises: a horizontal top wall 152, being part of the integral skirt and female luer connector 98; a cylindrical side wall 156 of the skirt; an internal second wall 158 which is parallel to the horizontal top wall 152 and is spaced therefrom: a filter 160 in the chamber 161 enclosed by horizontal top wall, cylindrical side wall and internal second wall; and filter cap 163 covering the top surface of the filter. The filter is an anti-microbial filter known in the art, such as Whatman Grade HCO1, USP Class 6. the remaining parts wherein the numerals marked by prime (') denote like elements described in FIG. 21.

List of Reference Numbers Used

Vial 10 & 10'
Cylindrical side wall of vial 12 & 12'
Flat bottom portion of vial 14 & 14'
Liquid medicament in vial 15'
Neck portion of vial 16 & 16'
Rim portion of top of vial 18 & 18'
Open area of top portion of vial 20 & 20'
Stopper 22 & 22'
Vial access adapter 24 & 24'
Cylindrical side wall of vial access adapter 26 & 26'
Rim of cylindrical side wall 27 & 27'
Flat horizontal top wall of vial access adapter 28 & 28'
Protuberance on rim portion 29 & 29'
Vent holes in top wall of vial access adapter 30 & 30'
Threaded luer connector means 32 & 32'
Dual spikes 34, 34', 36 & 36'
Sharp points in dual spikes 38, 38', 40 & 40'
Flow passages in dual spikes 42, 42', 44 & 44'
Slots in cylindrical side wall 46 & 46'
Elastomeric seal/membrane, M-shaped diaphragm 48 & 48'
U-shaped diaphragm 49 & 49'
Internal second wall 50 & 50'
Chamber 51 & 51'
Filter 52
Leg portion of M-shaped membrane 54
Cup-shaped portion of M-shaped membrane 56
Horizontal bottom portion of cup-shaped portion 58
Side portion of cup-shaped portion 60
Slit in bottom portion 62
Top surface of cup-shaped portion 64
Bottom surface of cup-shaped portion 66
Unpenetrated portion of membrane 68
Luer connector (external) 70
Cylindrical cap of luer connector 72
Tubing conduit of luer connector 74
Inside wall of cylindrical cap 76
Threads on inside wall of cylindrical cap 78
Bottom end portion of tubing conduit 80
Vial and protective container, generally designated 82
Vial with V-shaped bottom 84
Medicinal fluid, generally designated 86
Cylindrical side wall of vial 88
Constricted neck portion of vial 90
Rim of vial 92
Open area of rim 94
Elastomeric stopper 96
Integral skirt and female luer connector, generally designated 98
Fluid removal rube 100
Luer cap 102
V-shaped bottom of vial, generally designated 104
Horizontal bottom portion of V-shape 106
Side portion of V-shape 108, 108'
Protective container, generally designated 110
Horizontal bottom wall of protective container 112
Vertical side walls of protective container 114, 114'
Top wall or cover of protective container 116

Hinge means of top wall or cover of protective container 118
Male portion of the luer connecting device, generally designated 120
Outside wall of male portion 122
Threads on the inside wall of male portion 124
Tube of the male portion 126
Channel in tube of male portion 127
Skirt of female luer connector 128
Female luer connector, generally designated 130
Inside wall of female fitting 132
Channel in female fitting 134
Groove in the bottom portion of the female luer fitting 136
Outside wall of female fitting with threads 138
Wide top portion of fluid removal tube 140
Tube fluid pathway 142
Terminating profile of fluid removal tube 144
Top surface of medicinal fluid 86 146
Bottom surface of medicinal fluid 86 148
Vent holes 150
Horizontal top wall of skirt 152
Fluid removal tube 154
Cylindrical side wall of skirt 156
Internal second wall 158
Filter 160
Chamber 161
Filter cap 163

Various modifications of the present invention disclosed will become apparent to those skilled in the art. This invention is intended to include such modifications to be limited only by the scope of the claims.

What is claimed is:

1. A vial access adapter-vial assembly allowing withdrawal of a nuclear drug contained in the vial without inverting the vial comprising:

(a) a vial having a nuclear drug therein; and (b) a vial access adapter body;

wherein said vial comprises:

a cylindrical side wall having a distal end and a proximal end, said distal end extending into a constricted neck portion terminating in a rim and defining an open fluid port, and said proximal end being closed by a flat outside bottom portion and a V-shaped inside bottom portion; said fluid port being closed by an elastomeric stopper; wherein said vial access adapter body comprises:

a cylindrical wall having a distal end and a proximal end terminating in a rim;

a flat, horizontal top wall closing the distal end of the cylindrical side wall and having vent holes therein;

a horizontal second wall parallel to said horizontal top wall and spaced therefrom, said horizontal top wall, second wall and cylindrical side wall enclosing a chamber designed to hold a filter therein;

an antibacterial filter contained in said chamber;

an externally threaded female luer connector projecting vertically above the horizontal top wall for receiving an internally threaded male luer connector of a syringe or cartridge;

an elongated spike having a fluid flow channel therein, and being integral with said female luer connector, extending into said vial and reacting the V-shaped bottom portion thereof to allow withdrawl of essentially all the medical fluid from the vial when said vial is in the right-side-up position, and a removable luer cap hermetically sealing the female luer connector, said removable luer cap acting as a protective cover and being made of lead.

2. A vial access adapter-vial assembly allowing withdrawal of a nuclear drug contained in the vial without inverting the vial comprising:

(a) a vial having a nuclear drug therein; and (b) a vial access adapter body;

wherein said vial comprises:

a cylindrical side wall having a distal end and a proximal end, said distal end extending into a constricted neck portion terminating in a rim and defining an open fluid port, and said proximal end being closed by a flat outside bottom portion and a V-shaped inside bottom portion; said fluid port being closed by an elastomeric stopper; wherein said vial access adapter body comprises:

a cylindrical wall having a distal end and a proximal end terminating in a rim;

a flat, horizontal top wall closing the distal end of the cylindrical side wall and having vent holes therein;

a horizontal second wall parallel to said horizontal top wall and spaced therefrom, said horizontal top wall, second wall and cylindrical side wall enclosing a chamber designed to hold a filter therein;

an antibacterial filter contained in said chamber;

an externally threaded female luer connector projecting vertically above the horizontal top wall for receiving an internally threaded male luer connector of a syringe or cartridge;

an elongated spike having a fluid flow channel therein, and being integral with said female luer connector, extending into said vial and reacting the V-shaped bottom portion thereof to allow withdrawl of essentially all the medical fluid from the vial when said vial is in the right-side-up position, and a removable luer cap hermetically sealing the female luer connector, said removable luer cap acting as a protective cover and being made of an alloy comprising lead.

* * * * *